United States Patent
Stix

(10) Patent No.: US 9,463,296 B2
(45) Date of Patent: Oct. 11, 2016

(54) LARYNGEAL MASK WITH PIRIFORM-FOSSA CONDUIT

(71) Applicant: Michael S. Stix, Lexington, MA (US)

(72) Inventor: Michael S. Stix, Lexington, MA (US)

( * ) Notice: Subject to any disclaimer, the term of this patent is extended or adjusted under 35 U.S.C. 154(b) by 75 days.

(21) Appl. No.: 14/551,150

(22) Filed: Nov. 24, 2014

(65) Prior Publication Data

US 2015/0128946 A1 May 14, 2015

Related U.S. Application Data

(60) Provisional application No. 61/973,791, filed on Apr. 1, 2014.

(51) Int. Cl.
*A61M 16/04* (2006.01)

(52) U.S. Cl.
CPC ..... *A61M 16/0415* (2014.02); *A61M 16/0409* (2014.02); *A61M 16/0486* (2014.02)

(58) Field of Classification Search
CPC ........... A61M 16/04; A61M 16/0402; A61M 16/0409; A61M 16/0415; A61M 16/0427; A61M 16/0431; A61M 16/0434; A61M 16/0463; A61M 16/0484; A61M 16/0486; A61M 16/0488; A61M 2039/082; A61M 2210/065; A61M 2210/0656; A61M 2210/1046; A61M 2210/105; A61M 2210/1053
USPC .......... 128/200.26, 207.14, 207.15; 600/120, 600/194; 604/96.01, 103.07, 514
See application file for complete search history.

(56) References Cited

U.S. PATENT DOCUMENTS

| 4,509,514 A | 4/1985 | Brain |
| 4,995,388 A | 2/1991 | Brain |
| 5,241,956 A | 9/1993 | Brain |
| 5,249,571 A | 10/1993 | Brain |
| 5,282,464 A | 2/1994 | Brain |

(Continued)

FOREIGN PATENT DOCUMENTS

| CN | 201436038 U | 4/2010 |
| WO | WO2009035365 A1 | 3/2009 |
| WO | 2012127434 A2 | 9/2012 |

OTHER PUBLICATIONS

US Patent and Trademark Office, International Search Report and Written Opinion for PCT/US2015/013239 (corresponding PCT application) (May 6, 2015).

(Continued)

*Primary Examiner* — Tan-Uyen (Jackie) T Ho
*Assistant Examiner* — Joseph D Boecker
(74) *Attorney, Agent, or Firm* — Modern Times Legal; Robert J. Sayre

(57) ABSTRACT

A laryngeal mask airway device inserted in the pharynx of an unconscious patient to ventilate the lungs includes an airway tube and mask portion with cuff formation shaped to fit the actual and potential space surrounding the circumference of the inlet to the larynx. A piriform-fossa conduit is included in a cuff formation of such mask to facilitate insertion of orogastric tubes. Anatomically the piriform-fossa conduit travels around the laryngeal inlet through the piriform fossa to reach the upper esophagus. Structurally the piriform-fossa conduit travels through the lateral cuff formation with the inflatable cuff element. The distal orifice of the piriform-fossa conduit is on the outer perimeter of the cuff formation near the tip of the mask, does not intersect the medial line at the tip, and does not increase bulk in the distal cuff formation along the medial line.

9 Claims, 28 Drawing Sheets

(56) References Cited

U.S. PATENT DOCUMENTS

| | | | |
|---|---|---|---|
| 5,297,547 | A | 3/1994 | Brain |
| 5,303,697 | A | 4/1994 | Brain |
| 5,305,743 | A | 4/1994 | Brain |
| 5,355,879 | A | 10/1994 | Brain |
| 5,391,248 | A | 2/1995 | Brain |
| 5,584,290 | A | 12/1996 | Brain |
| 5,632,271 | A | 5/1997 | Brain |
| 5,682,880 | A | 11/1997 | Brain |
| 5,878,745 | A | 3/1999 | Brain |
| 5,896,858 | A | 4/1999 | Brain |
| 5,937,860 | A | 8/1999 | Cook |
| 6,079,409 | A | 6/2000 | Brain |
| 6,439,232 | B1 | 8/2002 | Brain |
| 6,631,720 | B1 | 10/2003 | Brain |
| 6,705,318 | B1 | 3/2004 | Brain |
| 6,705,321 | B2 | 3/2004 | Cook |
| 7,004,169 | B2 | 2/2006 | Brain |
| 7,040,322 | B2 | 5/2006 | Fortuna |
| 7,357,845 | B2 | 4/2008 | Cook |
| 7,780,900 | B2 | 8/2010 | Cook |
| 7,900,632 | B2 | 3/2011 | Cook |
| 7,997,274 | B2 | 8/2011 | Baska |
| 8,215,307 | B2 | 7/2012 | Nasir |
| 8,590,535 | B2 | 11/2013 | Dubach |
| 2005/0081861 | A1* | 4/2005 | Nasir .................. A61M 16/04 128/207.14 |
| 2006/0180156 | A1* | 8/2006 | Baska .................. A61M 16/04 128/207.15 |
| 2006/0207601 | A1* | 9/2006 | Nasir .................. A61M 16/04 128/207.14 |
| 2010/0319704 | A1 | 12/2010 | Nasir |
| 2011/0023890 | A1* | 2/2011 | Baska .................. A61M 16/04 128/207.15 |
| 2012/0090609 | A1 | 4/2012 | Dubach |
| 2012/0174929 | A1 | 7/2012 | Esnouf |
| 2012/0211010 | A1 | 8/2012 | Brain |
| 2013/0125897 | A1 | 5/2013 | Baska |
| 2013/0324798 | A1* | 12/2013 | Molnar .................. A61M 16/04 600/120 |
| 2014/0000624 | A1 | 1/2014 | Miller |

OTHER PUBLICATIONS

Akhtar, "Oesophageal vent-laryngeal mask to prevent aspiration of gastric contents," 72 Br. J. Anaesth. 52-54 (1994).
Asai, "Editorial II: Who is at increased risk of pulmonary aspiration?," 93 Br. J. Anaesth. 497-500 (2004).
Brain, et al., "The LMA 'ProSeal'—a laryngeal mask with oesophageal vent," 84 Br. J. Anaesth. 650-654 (2000).
Brimacombe, et al., "Mechanical airway obstruction after cricoid pressure with the laryngeal mask airway," 78 Anesth Analg. 604-605 (1994).
Brimacombe, "Laryngeal mask anesthesia: Principles and practice, 2nd edition," Saunders, Philadelphia, Chapter 1 (History), 1-41 (2005).
Brimacombe, "Laryngeal mask anesthesia: Principles and practice, 2nd edition," Saunders, Philadelphia, Chapter 19 (ProSeal LMA for ventilation and airway protection, I), 505-539 (2005).
Brimacombe, "Laryngeal mask anesthesia: Principles and practice, 2nd edition," Saunders, Philadelphia, Chapter 22 (Other extraglottic airway devices), 577-633 (2005).
Brimacombe, et al., "Mechanical closure of the vocal cords with the laryngeal mask airway ProSeal," 88 Br. J. Anaesth. 296-297 (2002).
Chan, et al., "Vocal cord paralysis after laryngeal mask airway ventilation," 115 Laryngoscope 1436-1439 (2005).
Cook, et al., "Analysis of 1000 consecutive uses of the ProSeal laryngeal mask airway by one anesthetist at a district general hospital," 99 Br. J. Anaesth. 436-439 (2007).
Cormier, et al., "Airflow in unilateral vocal cord paralysis before and after Teflon injection," 33 Thorax 57-61 (1978).
Goldmann, et al., "Use of ProSeal laryngeal mask airway in 2114 patients: A prospective study," 107 Anesth Analg 1856-1861 (2008).
Hernandez, et al., "Evolution of the extraglottic airway: A review of its history, applications, and practical tips for success," 114 Anesth Analg 349-368 (2012).
Keller, et al., "Aspiration and the laryngeal mask airway: three cases and a review of the literature," 93 Br. J. Anaesth. 579-582 (2004).
Lemere, "Innervation of the larynx," 18 Arch Otolaryngology 413-424 (1933).
The Laryngeal Mask Company Limited, LMA Airway Instruction Manual (2005).
Negus, "The mechanism of the larynx," 10 The Laryngoscope 961-986 (1957).
O'Connor, et al., "Gastric distention in a spontaneously ventilating patient with a ProSeal laryngeal mask airway," 94 Anesth Analg 1656-1658 (2002).
O'Connor, et al., "Assessing ProSeal Laryngeal Mask Positioning: The Suprasternal Notch Test," 94 Anesth Analg 1374-1375 (2002).
Pennant, et al., "The laryngeal mask airway: Its uses in anesthesiology," 79 Anesthesiology 144-163 (1993).
Ramachandran, et al., "Predictors and clinical outcomes from failed laryngeal mask airway Unique," 116 Anesthesiology 1217-1226 (2012).
Russo, et al., "Magnetic resonance imaging study of the in vivo postion of the extraglottic airway devices i-gel and LMA-Supreme in anaesthetized human volunteers," 109 Br. J. Anaesth. 996-1004 (2012).
Stix, et al., "Esophageal aspiration of air through the drain tube of the ProSeal laryngeal mask," 93 Anesth Analg 1354-1357 (2001).
Stix, et al., "Depth of insertion of the ProSeal laryngeal mask airway," 90 Br J Anaesth 235-237 (2003).
Stix, et al., "Maximum minute ventilation test for the ProSeal laryngeal mask airway," 95 Anesth Analg 1782-1787 (2002).
Stix, et al., "The ProSeal LMA does not cause laryngeal edema," 53 Can J Anesth 961-963 (2006).
Timmerman, et al., "Prospective clinical and fiberoptic evaluation of the Supreme laryngeal mask airway," 110 Anesthesiology 262-265 (2009).
van Zundert, et al., "Archie Brain: celebrating 30 years of development in laryngeal mask airways," 67 Anaesthesia 1375-1385 (2012).

\* cited by examiner

LARYNGEAL MASK WITH PIRIFORM-FOSSA CONDUIT

RELATED APPLICATION

This application claims the benefit of U.S. Provisional Application No. 61/973,791, filed 1 Apr. 2014, the entire content of which is incorporated herein by reference.

BACKGROUND

The invention relates to a laryngeal mask airway device used in unconscious patients to ventilate the lungs having an airway tube opening into the interior of a firm recessed ovoid bowl having attached at its periphery a cuff formation shaped to fit the actual and potential space surrounding the circumference of the inlet to the larynx. The cuff formation commonly takes the form of an inflatable cuff. The laryngeal mask is inserted into the unconscious patient's pharynx and is advanced until its tip is positioned within the upper esophagus and the cuff formation surrounds the circumference of the inlet to the larynx. The airway tube with the opening in the firm recessed bowl of the mask is then aligned with the laryngeal inlet to provide ventilation to the lungs.

FIG. 1 depicts a perspective view of a laryngeal mask 60 with a cuff formation in the form of an inflatable cuff 64. The laryngeal mask comprises two portions, an airway tube 62 and a mask portion 61 consisting of a bowl structure 68 that helps define a recessed interior space of the bowl structure 68 and a cuff formation that is an inflatable cuff 64 attached at a periphery of the bowl structure 68. The airway tube 62 has a proximal orifice 72 with suitable adapter for connection to respiratory equipment. The airway tube 62 is joined to the mask portion 61 and has fluid communication with an aperture 74 within the recessed ovoid bowl 68 of the laryngeal mask 60. The inflatable cuff 64 can be filled with fluid through an inflation line 76 with a pilot balloon/one-way valve 78 and the cuff formation (here depicted as an inflatable cuff 64) forms a seal with the pharynx surrounding the circumference of the inlet to the larynx.

FIG. 2A is a front view of a mask portion 61 with bowl structure 68 and cuff formation. FIG. 2A depicts descriptors for the different portions of a cuff formation, including proximal portion 80, lateral portion 82, and distal portion 84. Also identified are the midline most proximal point 85 of the cuff formation and the midline most distal point 86 of the cuff formation.

FIG. 2B is a front view of the same mask portion 61 as in FIG. 2A and depicts length measurements. FIG. 2B depicts the entire length 126 of the mask portion 61, the length 130 of the distal one-half of the mask portion 61, and the length 132 of the distal one-third of the mask portion 61.

FIG. 2C is a front view of the same mask portion 61 as in FIG. 2A and depicts a medial line 136 that passes through the midline most proximal point 85 of the mask portion 61 and through the midline most distal point 86 of the mask portion 61. FIG. 2C also depicts a midway-dividing line 138 corresponding to the length measurement 130 and dividing the mask portion into a proximal half 140 and a distal half 142. The distal one-third of the mask portion corresponding to the length measurement 132 is indicated by a demarcation line 139.

FIG. 3 depicts a side view of the anatomy of the human pharynx shown by dashed lines illustrating the anatomical relations of a laryngeal mask that is inserted in an unconscious patient. The distal portion 84 of the cuff formation is within the upper esophagus 18, contacting the mucosal surfaces of the esophageal walls 17, and the distal portion 84 lies directly behind the cricoid cartilage 15. The proximal portion 80 of the cuff formation rests against the base of the tongue 11. The epiglottis 12 may enter the recessed space of the bowl interior. The inflatable cuff 64 surrounds the laryngeal inlet 13 that leads to the vocal cords 14 and the trachea 16. The airway tube 62 emerges from the mouth 10 and may be connected to respiratory equipment.

FIG. 4 demonstrates a front view of human head and neck anatomy shown by dashed lines illustrating the anatomical relations of a laryngeal mask that is inserted in an unconscious patient. The inflatable cuff 64 and bowl structure 68 occupy the lower pharynx bounded laterally by pharyngeal walls 24 that funnel downwards forming esophageal walls 17 and the esophagus 18. The inflatable cuff 64 and bowl structure 68 lie posterior to the larynx with cricoid cartilage 15 and thyroid cartilage 23. The distal portion of the inflatable cuff 64 enters the esophagus 18 posterior to the cricoid cartilage 15. The airway tube 62 comes out of the mouth 10 and may be connected to respiratory equipment. Superficial landmarks include the sternocleidomastoid muscles 20, clavicle bones 21, and manubrium of the sternum 22.

The laryngeal mask occupies the lower pharynx of an unconscious patient with an inflatable cuff 64 adapted to fit the space surrounding the circumference of the inlet to the larynx. The airway tube 62 provides respiratory gases through its distal orifice within the recessed bowl structure 68 that is located opposite the laryngeal inlet leading to the lungs. The laryngeal mask airway device occupies the lower pharynx and upper esophagus but does not go through the vocal cords into the trachea; consequently, the laryngeal mask presents two potential problems.

First, if the vocal cords close for any reason, then the aperture or space or void between the two vocal cords (called the glottis or glottic space) may become extremely small or be abolished; and it may be difficult or impossible to provide ventilation for the patient despite correct positioning of the laryngeal mask. The vocal cords are located in the fluid channel for oxygen traveling through a laryngeal mask airway device to the lungs and the vocal cords form an aperture in such fluid channel for oxygen delivery to the lungs. It is possible for the area of the glottis to be sufficiently reduced or narrowed such that the ability of a laryngeal mask airway device to provide adequate oxygen and ventilation for an unconscious patient either by spontaneous ventilation or by positive pressure ventilation will be severely compromised.

Second, the laryngeal mask airway device is not as protective for the patient as is a cuffed endotracheal tube against pulmonary aspiration of gastric contents. Pulmonary aspiration of gastric contents describes the physical process of gastric contents, liquid or solid, entering the lungs, thereby obstructing the airway passages or damaging the delicate lung alveoli; and such pulmonary aspiration may be life-threatening or fatal for the patient. The cuffed endotracheal tube is an airway device that passes between the vocal cords into the trachea; and the portion of the endotracheal tube that enters the trachea may have an inflatable cuff that forms a seal with the interior walls of the trachea that may prevent gastric contents from contaminating the lower airways and lung alveoli. Since the laryngeal mask does not pass through the vocal cords, it does not provide such protection.

Previous inventions of laryngeal masks targeting the advantage of decreasing the risk of pulmonary aspiration of gastric contents have included a tube called an evacuation tube or drainage tube added to the laryngeal mask construction. Such evacuation tube or drainage tube has a distal orifice near the tip of the mask, travels through the tip of the mask parallel to the medial line, and arrives at the tip of the mask traveling in front of, within, or behind the back of the recessed ovoid interior space of the laryngeal mask bowl. The proximal orifice of the evacuation tube or drainage tube is adjacent to the proximal orifice of the airway tube. Following insertion of such mask, the distal orifice of the tube, positioned in the upper esophagus, can capture regurgitating gastrointestinal contents and, through the interior of the tube, evacuate gastrointestinal contents to the outside of the patient and away from the lungs. Such a tube that is part of the laryngeal mask construction can also facilitate insertion of orogastric tubes from outside the patient directly to the upper esophagus; and such orogastric tubes can be advanced into the esophagus and stomach in order to passively drain or to actively suction liquid gastrointestinal contents to outside the patient and to reduce the patient's risk for pulmonary aspiration of gastric contents.

Previous inventions of laryngeal masks targeting the advantage of decreasing the risk of pulmonary aspiration of gastric contents have enhanced the cuff formation to increase the seal pressure with the pharyngeal and esophageal mucosal surfaces, have added tubes and constructions extending beyond the tip of the cuff formation, and have included methods to occlude the esophageal lumen such as with esophageal blockers.

The first commercially available laryngeal mask with a drainage tube and specifically enhanced cuff formation was the PROSEAL laryngeal mask (from Teleflex Inc., North Carolina, USA) developed by Dr. Archibald J. Brain—see, e.g., U.S. Pat. Nos. 4,509,514; 5,241,956; and 6,439,232 B1; and Brain, et al., "The LMA 'ProSeal'—a laryngeal mask with an oesophageal vent," 84 Br. J. Anaesth. 650-654 (2000). The present inventor used this laryngeal mask in clinical practice of anesthesiology and performed research of the PROSEAL laryngeal mask. The present inventor investigated clinical characteristics of laryngeal mask design with the presence of a drainage tube passing through the central portion of the distal cuff formation and investigated clinical characteristics of laryngeal mask design with enhanced cuff formation.

SUMMARY

During clinical use of the PROSEAL laryngeal mask, the present inventor experienced cases where the drainage tube evacuated gastrointestinal liquid contents to outside the patient and provided protection from pulmonary aspiration of gastric contents. The present inventor also used the drainage tube to insert orogastric tubes and, by means of such orogastric tubes, to suction liquid gastrointestinal contents to outside the patient and provide protection from pulmonary aspiration of gastric contents.

Unfortunately, the clinical experience of the present inventor, when using the PROSEAL laryngeal mask in unconscious patients, was that severe problems with obstruction of the airway passages, making the provision of adequate oxygenation and ventilation difficult, occurred in a small but significant percentage of patients. In this small but significant percentage of patients, the present inventor exchanged the PROSEAL laryngeal mask for another airway device for provision of oxygenation and ventilation and for provision of anesthetic gases before the surgical procedure was started. The experience of the present inventor was reflected in a study of 2,114 patients that reported 3.3% incidence where the PROSEAL laryngeal mask was abandoned in favor of the endotracheal tube to provide ventilation of the lungs for the patient for the surgical operation [Goldmann, et al., "Use of ProSeal laryngeal mask airway in 2114 adult patients; a prospective study," 107 Anesth. Analg. 1856-1861 (2008)].

Using the PROSEAL laryngeal mask, the present inventor observed that the most frequent cause for severe obstruction of the airway passages was a dramatic narrowing of the aperture or space or opening between the vocal cords (i.e., a dramatic decrease in size of the glottis). The present inventor carried out investigations of the narrowing of the glottic opening by laryngeal mask shape, design, and construction with observations illustrated in FIGS. 5-7, further discussion of which continues in the Detailed Description.

A laryngeal mask of this disclosure can include a mask portion having a proximal end in a proximal half, a distal end in a distal half, and a medial line extending from the proximal end to the distal end centrally through the mask portion, wherein the mask portion has a bowl structure that helps to define a bowl interior that is concave toward an anterior-facing opening and a cuff formation attached to a periphery of the bowl interior or recess or interior space of the mask portion. An airway conduit with a distal orifice is coupled with, and in fluid communication with, the bowl interior proximate the proximal end of the bowl interior. The cuff formation includes a piriform-fossa conduit with a proximal orifice proximate the proximal orifice of the airway conduit and extending along a pathway ending on one side of the medial line and defining a distal orifice along an outer perimeter of the cuff formation proximate the distal end of the mask portion and within the distal one-third of the mask portion, and wherein the distal orifice is non-intersecting with the medial line, and wherein the piriform-fossa conduit is an element of the cuff formation of the mask portion, wherein the piriform-fossa conduit travels in the lateral portion of the cuff formation, wherein in the distal one-half of the mask portion of the laryngeal mask, the piriform-fossa conduit travels only in the cuff formation, and wherein the proximal orifice of the piriform-fossa conduit opens to an exterior environment outside the laryngeal mask, and wherein the distal orifice of the piriform-fossa conduit opens to an exterior environment outside the laryngeal mask.

In a method for installing an artificial airway in a patient, a laryngeal mask, as described above, is inserted into a patient's pharynx. The tip of the laryngeal mask is advanced within the pharynx into the patient's esophageal inlet, and the cuff formation occupies the space surrounding the circumference of the inlet to the larynx. A gas including oxygen is flowed through the airway conduit into the bowl interior, from where the oxygen is delivered through the inlet to the larynx and through the vocal cords to the lungs of the patient. Finally, the piriform-fossa conduit is positioned in a piriform fossa of the patient with the proximal orifice opening outside of the patient's mouth and the distal orifice opening to the esophageal inlet.

Embodiments of the laryngeal mask and the use thereof can provide any or all of the following advantages.

First, the laryngeal mask can be advantageously used in unconscious patients to ventilate the lungs via an airway tube with a proximal orifice located outside of the mouth, wherein the proximal orifice of the airway tube may be connected to respiratory equipment, and wherein a distal orifice opens into the interior of a firm ovoid bowl having attached at its periphery a cuff formation shaped to fit the actual and potential space surrounding the circumference of the inlet to the larynx. The cuff formation can include a piriform-fossa conduit with a proximal orifice proximate the proximal orifice of the airway conduit, traversing a pathway through the lateral portion of the cuff formation, and with a distal orifice along an outer perimeter of the cuff formation proximate the distal end of the mask portion and within the distal one-third of the mask portion, wherein the distal orifice is non-intersecting with the medial line.

Additional advantages may include any or all of the following:

- the distal portion of the cuff formation along the medial line can be thin and compliant;
- the piriform-fossa conduit does not travel along the medial line posterior to the cricoid cartilage and does not displace the cricoid cartilage in an anterior direction;
- the cuff formation can conform to the actual and potential space surrounding the circumference of the inlet to the larynx and avoid severe compression of the glottic opening;
- the piriform-fossa conduit can direct the insertion of orogastric tubes or medical instruments from outside the patient to the esophageal inlet completely within the interior of the piriform-fossa conduit;
- the piriform-fossa conduit can direct the insertion of orogastric tubes or medical instruments from outside the patient to the esophageal inlet through a piriform fossa of the patient;
- the piriform-fossa conduit can direct the insertion of esophageal blocker devices from outside the patient to the esophageal inlet completely within the interior of the piriform-fossa conduit;
- the piriform-fossa conduit can direct the insertion of orogastric tubes from outside the patient to the esophageal inlet completely within the interior of the piriform-fossa conduit and such orogastric tubes can be further advanced into the patient's gastrointestinal tract and be used to passively drain or actively suction liquid gastrointestinal contents from inside the esophagus or stomach or small intestines to the exterior of the patient;
- the patient's risk of pulmonary aspiration of liquid gastrointestinal contents can be reduced;
- the piriform-fossa conduit in a cuff formation can be formed of a soft and flexible medically approved biocompatible polymeric material such as soft and flexible polyvinyl chloride (PVC) or silicone rubber;
- the piriform-fossa conduit may be joined to other elements of the laryngeal mask airway device by welding, fitting, mechanical fastening, or adhesive methods;
- the distal extent of the piriform-fossa conduit may be partially collapsed by pharyngeal tissues and still be able to accommodate and direct insertion of orogastric tubes or medical instruments from outside the patient to the esophageal inlet;
- a piriform-fossa conduit in a cuff formation can be formed of soft and flexible material and can allow non-traumatic insertion of the laryngeal mask into the pharynx;
- a piriform-fossa conduit in a cuff formation can be formed of soft and flexible material and can avoid increased incidence of sore throat in the patient;
- a piriform-fossa conduit in a cuff formation can be formed of soft and flexible material and can avoid increased incidence of nerve injury of the pharynx or larynx;
- a sealed entry with an inflatable cuff element of the cuff formation can preserve the inflation integrity of the inflatable cuff component;
- a sealed exit with an inflatable cuff element of the cuff formation can preserve the inflation integrity of the inflatable cuff component;
- a piriform-fossa conduit may be the only element in a portion of the cuff formation.
- a mount coupling can provide mechanical stability to the piriform-fossa conduit proximate the proximal end of the mask portion;
- the mount coupling can be bonded to the bowl structure of the mask portion of the laryngeal mask or it may be manufactured as part of the bowl structure;
- the mount coupling can be bonded to the airway tube or manufactured as part of the airway tube;
- a segment of the piriform-fossa conduit can be bonded to the airway tube or manufactured as part of the airway tube;
- a mount coupling can join two segments of piriform-fossa conduit of different material characteristics while preserving the airtight integrity of the piriform-fossa conduit walls and preserving patency of the conduit lumen;
- a segment of the piriform-fossa conduit in the cuff formation can be formed of a soft and flexible material, and a segment of the piriform-fossa conduit not in the cuff formation can be formed of a harder and less flexible material;
- a piriform-fossa conduit may have a cross-sectional profile that is not circular and still be able to accommodate and direct insertion of medical instruments from outside the patient to the esophageal inlet;
- a piriform-fossa conduit may have a cross-sectional profile that changes throughout its length and that is still be able to accommodate and direct insertion of medical instruments from outside the patient to the esophageal inlet;
- a plug structure may be reversibly inserted into the proximal orifice of the piriform-fossa conduit to occlude the orifice and may be removed from the proximal orifice of the piriform-fossa conduit so that the proximal orifice is open;
- an attachment length can be included to secure the plug structure to the outside of piriform-fossa conduit in the vicinity of the proximal orifice;
- the plug structure can be prevented from falling into the proximal orifice of the airway tube; and
- respiratory gases, oxygen and anesthetic gases can be prevented from escaping or venting from the pharynx to the exterior of the patient by fluid flow through the lumen of the piriform-fossa conduit;

BRIEF DESCRIPTION OF THE DRAWINGS

In the accompanying drawings, like reference characters refer to the same or similar parts throughout the different views. The drawings are not necessarily to scale, emphasis instead being placed upon illustrating particular principles, discussed below.

DETAILED DESCRIPTION

Figure 1:
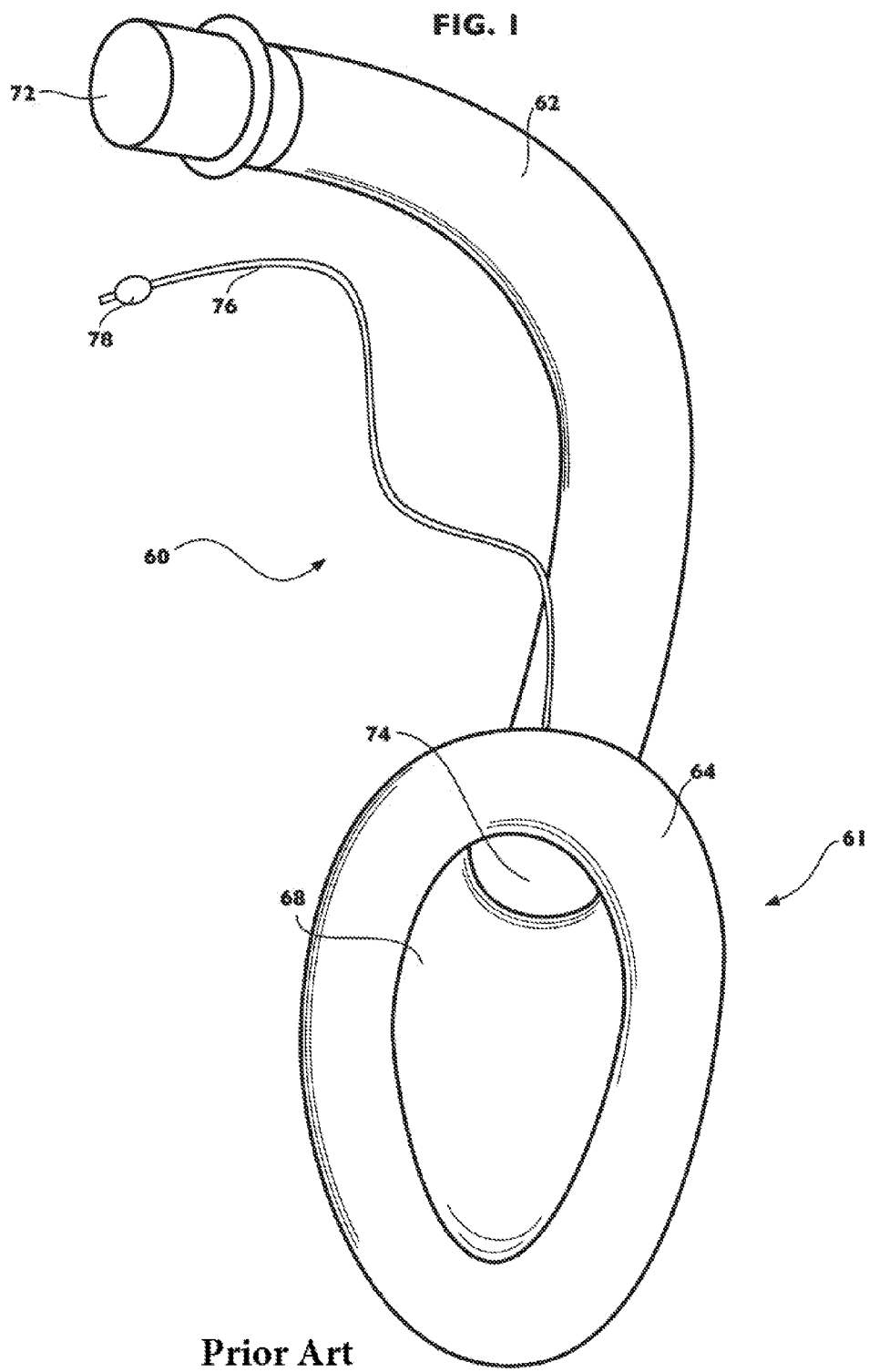
FIG. 1 is a perspective view of a laryngeal mask.
Figure 2A:
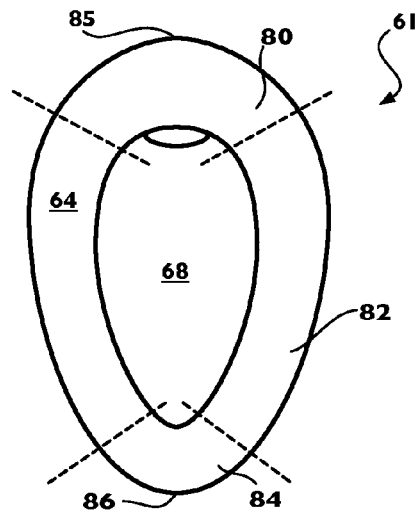
FIGS. 2A-C are front views of a mask portion of a laryngeal mask.
Figure 2B:
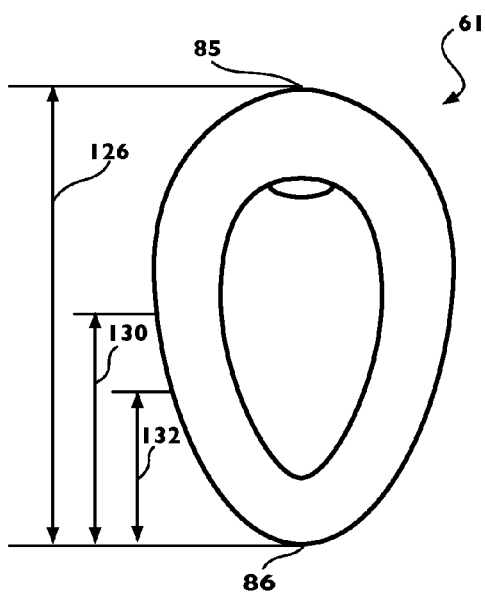
Figure 2C:
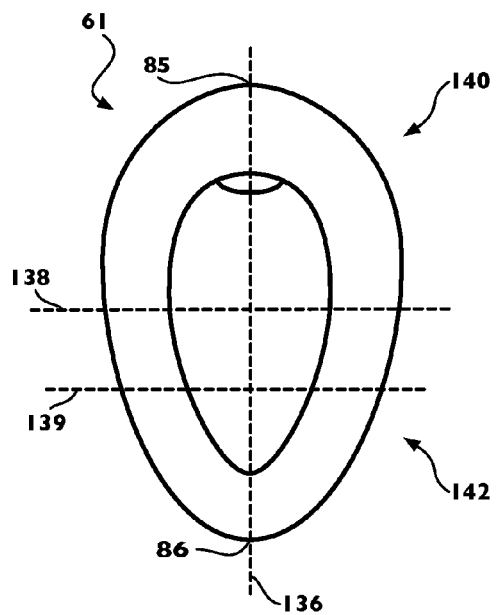
Figure 3:
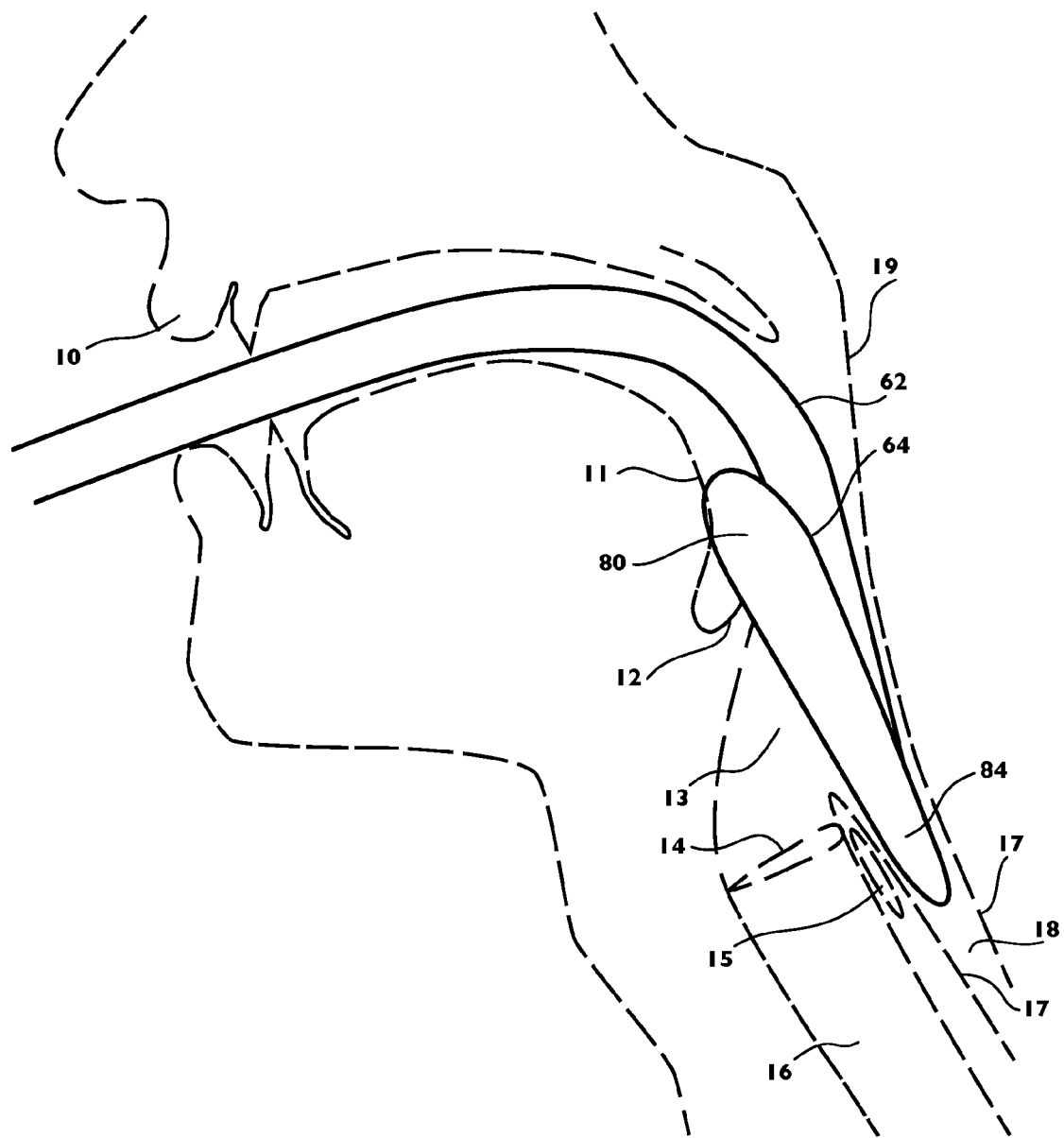
FIG. 3 is a side view of the anatomy of the pharynx shown by dashed lines illustrating the anatomical relations of a laryngeal mask that is inserted in an unconscious patient.
Figure 4:
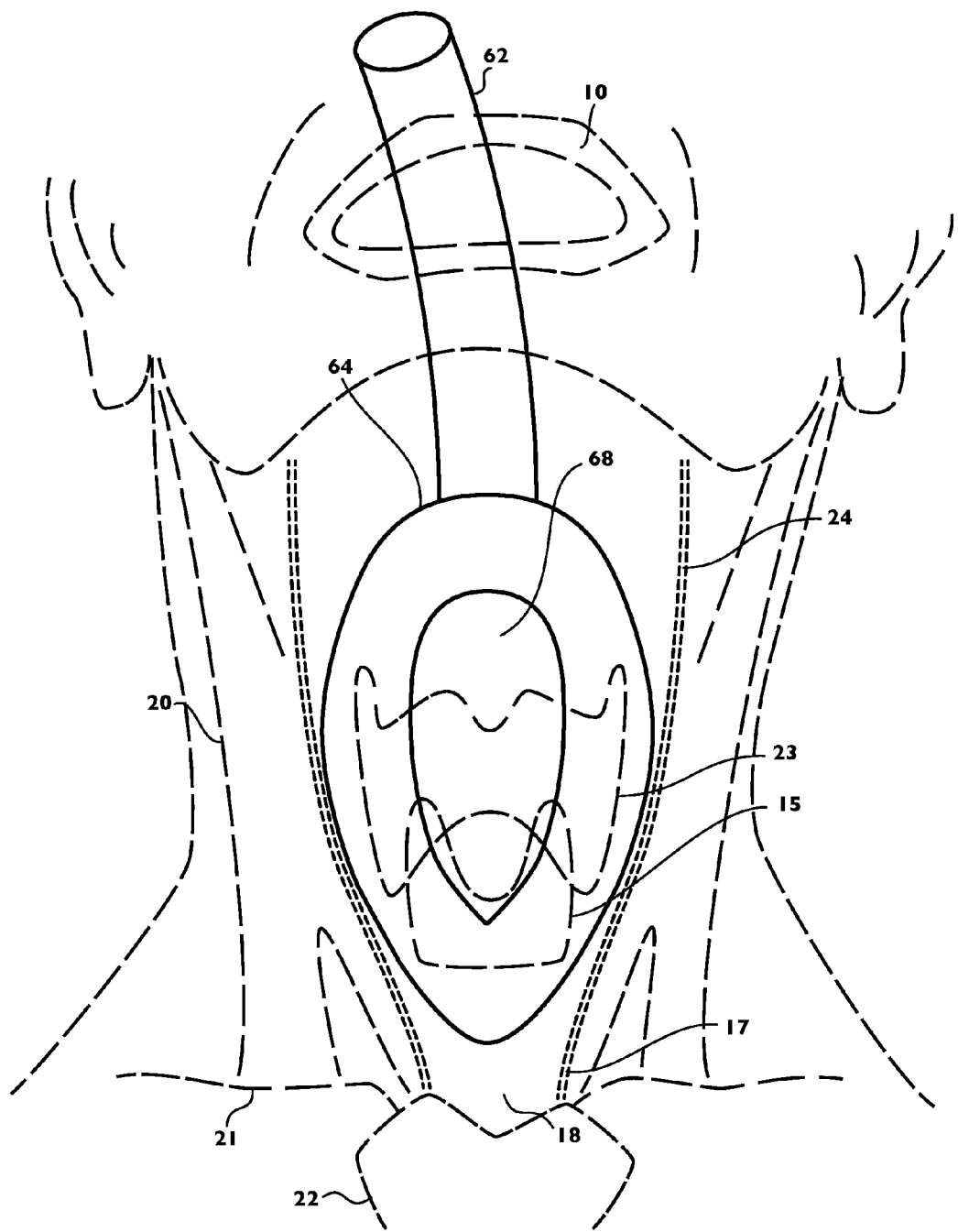
FIG. 4 is a front view of human head and neck anatomy shown by dashed lines illustrating the anatomical relations of a laryngeal mask that is inserted in an unconscious patient.

The foregoing and other features and advantages of various aspects of the invention(s) will be apparent from the following, more-particular description of various concepts and specific embodiments within the broader bounds of the invention(s). Various aspects of the subject matter introduced above and discussed in greater detail below may be implemented in any of numerous ways, as the subject matter is not limited to any particular manner of implementation. Examples of specific implementations and applications are provided primarily for illustrative purposes.

Unless otherwise defined, used or characterized herein, terms that are used herein (including technical and scientific terms) are to be interpreted as having a meaning that is consistent with their accepted meaning in the context of the relevant art and are not to be interpreted in an idealized or overly formal sense unless expressly so defined herein. For example, if a particular composition is referenced, the composition may be substantially, though not perfectly pure, as practical and imperfect realities may apply; e.g., the potential presence of at least trace impurities (e.g., at less than 1 or 2%) can be understood as being within the scope of the description; likewise, if a particular shape is referenced, the shape is intended to include imperfect variations from ideal shapes, e.g., due to manufacturing tolerances. Percentages or concentrations expressed herein can represent either by weight or by volume. Processes, procedures and phenomena described below can occur at ambient pressure (e.g., about 50-120 kPa—for example, about 90-110 kPa) and temperature (e.g., −20 to 50° C.—for example, about 10-35° C.).

Although the terms, first, second, third, etc., may be used herein to describe various elements, these elements are not to be limited by these terms. These terms are simply used to distinguish one element from another. Thus, a first element, discussed below, could be termed a second element without departing from the teachings of the exemplary embodiments.

All spatially relative terms such as "superior," "inferior," "anterior," "posterior," "left," "right," medial," "lateral," and the like, are defined by the anatomical position commonly accepted in the study of human anatomy. Terms for anatomical sections such as "coronal," "sagittal," "midsagittal," "median," "transverse", "horizontal," and the like, are also defined by the anatomical position commonly accepted in the study of human anatomy.

Further still, in this disclosure, when describing an artificial airway device, it is assumed that the device has been correctly inserted in an unconscious patient and that the device is in a proper anatomical position. The spatially relative term, "proximal," will refer to the direction along the airway device in the direction of the source of oxygen delivery by respiratory equipment located outside the patient. The spatially relative term, "distal," will refer to the direction along the airway device in a direction towards the feet. The spatially relative term, "anterior," will refer to a direction in the artificial airway device in an anterior direction within the human body at its location. Finally, the spatially relative term "posterior" will refer to a direction the artificial airway device in a posterior direction within the human body at its location.

Further still, in this disclosure, when an element is referred to as being "on," "connected to," "coupled to," "in contact with," etc., another element, it may be directly on, connected to, coupled to, or in contact with the other element or intervening elements may be present unless otherwise specified.

The terminology used herein is for the purpose of describing particular embodiments and is not intended to be limiting of exemplary embodiments. As used herein, singular forms, such as "a" and "an," are intended to include the plural forms as well, unless the context indicates otherwise. Additionally, the terms, "includes," "including," "comprises" and "comprising," specify the presence of the stated elements or steps but do not preclude the presence or addition of one or more other elements or steps.

Additionally, the various components identified herein can be provided in an assembled and finished form; or some or all of the components can be packaged together and marketed as a kit with instructions (e.g., in written, video or audio form) for assembly and/or modification by a customer to produce a finished product.

The following list of reference numbers identifies parts that are illustrated in the drawings:

LIST OF REFERENCE NUMBERS 10 mouth
11 base of tongue
12 epiglottis
13 laryngeal inlet
14 vocal cord
15 cricoid cartilage
16 trachea
17 esophagus wall
18 esophagus
19 posterior pharyngeal wall
20 sternocleidomastoid muscle
21 clavicle
22 manubrium of sternum
23 thyroid cartilage
24 lateral pharyngeal wall
25 piriform fossa
26 interarytenoid notch
27 arytenoid cartilage
28 cuneiform tubercle
29 aryepiglottic fold
30 glottis
31 vocal process of arytenoid cartilage
32 muscular process of arytenoid cartilage
33 posterior glottic chink
34 false vocal cords
35 position with inspiratory gas flow
36 pharynx
37 potential space underneath larynx resting on posterior pharyngeal wall
60 laryngeal mask
61 mask portion of laryngeal mask
62 airway tube
64 inflatable cuff
66 anterior surface of bowl
68 bowl structure
70 posterior surface of bowl
72 proximal orifice of airway tube
74 aperture inside bowl in fluid communication with airway tube
76 inflation line
78 pilot balloon/one-way valve
80 proximal portion of the cuff formation
82 lateral portion of the cuff formation
84 distal portion of the cuff formation
85 midline most proximal point of the cuff formation
86 midline most distal point of the cuff formation
88 conduit
90 proximal orifice of piriform-fossa conduit
92 piriform-fossa conduit
94 distal orifice of piriform-fossa conduit
96 sealed entrance with cuff
98 sealed exit with cuff
100 airway tube junction with bowl structure
102 mount coupling for piriform-fossa conduit
104 air or fluid filling inflatable cuff
106 concavity on anterior surface of bowl for entrance airway tube
108 junction of cuff structure and bowl structure
110 interior or lumen of piriform-fossa conduit
112 junction of cuff with front of bowl structure
114 plug structure
116 attachment length for plug structure
118 bonding attachment length to plug structure
120 bonding attachment length to piriform-fossa conduit
124 bonding mount coupling piriform-fossa conduit to bowl structure
126 length of mask portion from proximal to distal
128 junction of cuff with back of bowl structure
130 length of distal one-half of mask portion from proximal to distal
132 length of distal one-third of mask portion from proximal to distal
134 thickness of distal cuff formation along the medial line in deflated state
136 medial line of mask portion
138 midway-dividing line dividing proximal and distal halves of mask portion
139 line demarcating distal one-third of mask portion
140 proximal half of mask portion
142 distal half of mask portion Henceforth, the term, "cuff formation of a laryngeal mask," will be used to describe the element or elements forming an approximately elliptical (typically, the outer perimeter of the construction is not a perfect ellipse but often with roughly the near-elliptical shape illustrated) flexible construction shaped to fit the actual and potential space surrounding the circumference of the inlet to the larynx and attached to a periphery of a bowl structure of a laryngeal mask that helps to define a bowl interior that is concave toward an anterior-facing opening. The airway conduit of the laryngeal mask has a distal orifice in fluid communication with the bowl interior proximate the proximal end of the bowl interior. By this definition, the cuff formation may include an inflatable cuff and/or may include an element other than an inflatable cuff.

Henceforth, the term, "mask portion of a laryngeal mask," will be understood to include all elements of a laryngeal mask artificial airway device located distally to (and including) the most proximal point of the cuff formation.

Figure 5A:
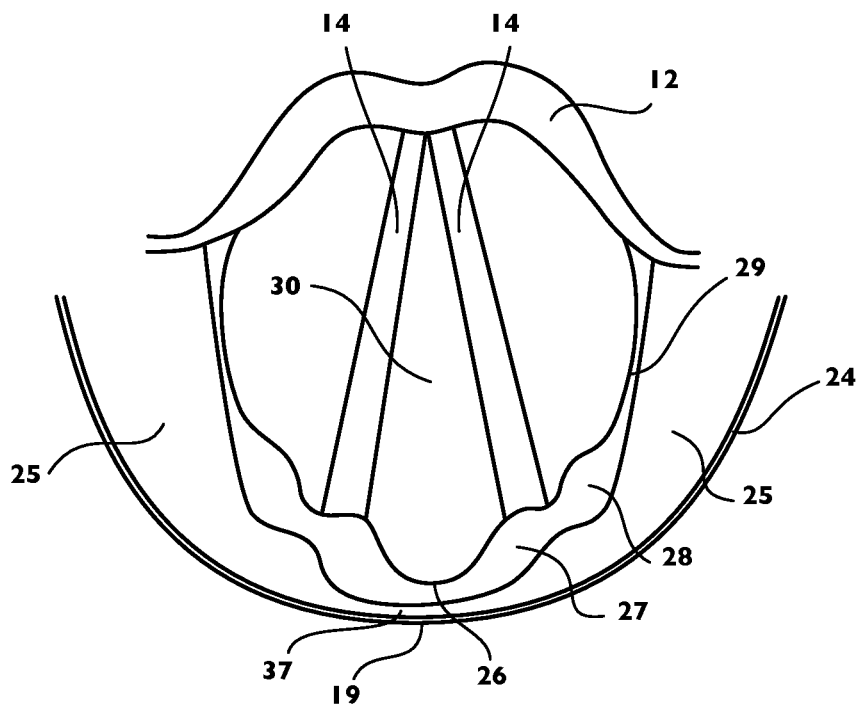
FIG. 5A is a view of the laryngeal inlet and laryngeal anatomy from the oropharynx in a resting state of a supine spontaneously ventilating patient without any artificial airway device.

Returning to the present inventor's observations, FIG. 5A depicts a view of the laryngeal inlet from the pharynx looking inferiorly in a resting state of a supine spontaneously ventilating patient without any artificial airway device. The oval-shaped circumference of the laryngeal inlet is defined by the epiglottis 12, aryepiglottic folds 29, cuneiform tubercle 28, arytenoid cartilage 27, and interarytenoid notch 26. Within the aperture of the laryngeal inlet and distal are the two vocal cords 14 and the space or void between them (i.e., the glottis 30, also called referred to as a glottic space 30). In this unperturbed state, the larynx and arytenoids 27 rest against the posterior pharyngeal wall 19 and define a narrow potential space 37 between the larynx and posterior pharyngeal wall 19; and the vocal cords 14 are widely separated with a large-sized glottis 30.

Figure 5B:
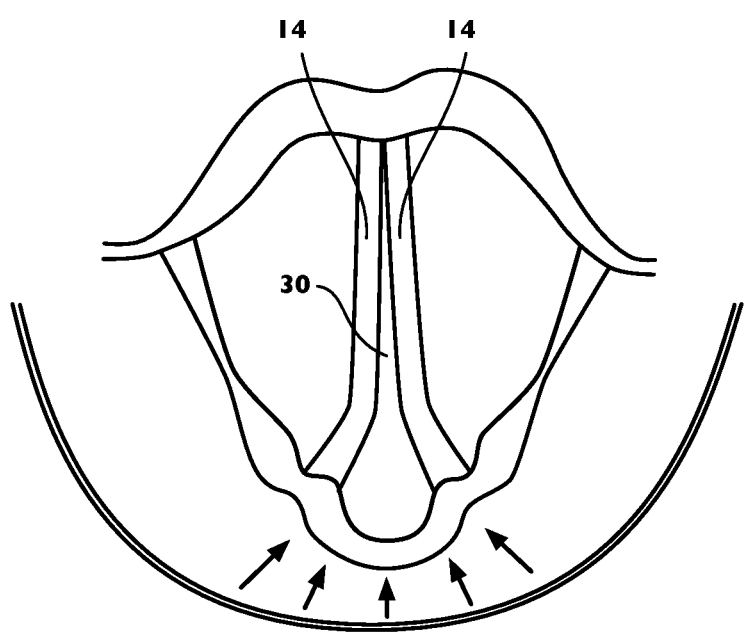
FIG. 5B is a view of the laryngeal inlet and laryngeal anatomy from the oropharynx when the shape of the inlet is narrowed and distorted by an embodiment of laryngeal mask entering the esophageal inlet in the space posterior to the larynx.

FIG. 5B depicts the laryngeal inlet viewed from the oropharynx when the shape of the laryngeal inlet is narrowed and distorted by displacement of the larynx in the anterior direction away from the posterior pharyngeal wall 19. Such displacement of the larynx in the anterior direction can occur with an embodiment of a laryngeal mask being inserted into the esophageal inlet and narrow space 37. Such anterior displacement of the larynx is most likely to occur when the distal cuff formation has a thick, bulky, and noncompliant nature along the medial line. When the larynx is so displaced in an anterior direction, the vocal cords 14 may be pushed together and the glottic space 30 may become severely narrowed. The arrows in FIG. 5B posterior to the laryngeal inlet indicate forces in an anterior direction by presence of an embodiment of laryngeal mask with thick distal cuff formation along the medial line.

FIG. 5A depicts two extensive spaces on both sides of the laryngeal inlet called the piriform fossa 25 (sometime spelled "pyriform fossa"). The piriform fossa 25 are lateral to the aryepiglottic folds 29 and funnel inferiorly to join the upper esophagus. By FIG. 5A there are three routes to reach the upper esophagus from the oropharynx, one route via the narrow space 37 posterior to the laryngeal inlet and two routes via the much larger piriform fossa channels lateral to the laryngeal inlet. A tube traveling to the upper esophagus via a piriform fossa will not displace the larynx anteriorly as in FIG. 5B.

Figure 6A:
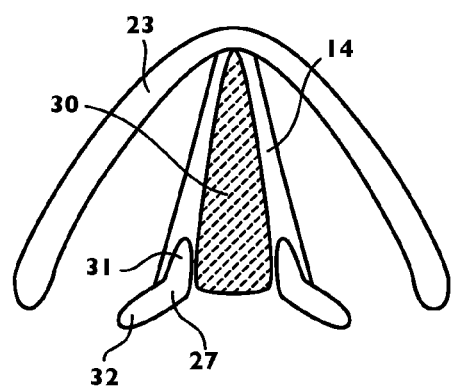
FIGS. 6A-C offer views of the anatomy of the vocal cords and of different positions of the vocal cords and glottis, looking inferiorly as from the interior of the recessed bowl of a laryngeal mask with a fiberoptic endoscopic instrument.
Figure 6B:
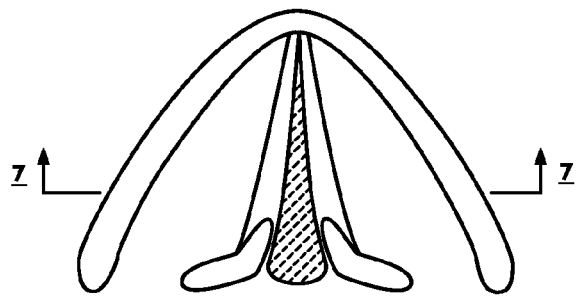
Figure 6C:
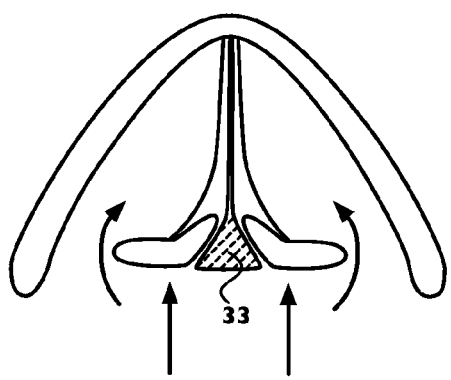

FIGS. 6A-C depict the anatomy of the vocal cords 14 and glottis 30. FIGS. 6A-C illustrate the vocal cords 14 attached anteriorly to the thyroid cartilage 23. The position of each vocal cord 14 is controlled by an arytenoid cartilage 27 that has vocal process 31 and muscular process 32; and FIGS. 6A-C illustrate how the position and rotation of the arytenoid cartilage 27 can dramatically impact the size of the glottic opening 30. FIG. 6A depicts the vocal cords 14 in a neutral position. FIG. 6B depicts arytenoid cartilages slightly rotated medially and a narrower glottis. FIG. 6C depicts arytenoid cartilages displaced anteriorly and rotated further medially and a dramatically reduced glottic opening, leaving a small posterior glottic chink 33. The arrows in FIG. 6C indicate forces exerted on the arytenoid cartilages by presence of an embodiment of laryngeal mask with a thick distal cuff formation along the medial line.

The experience of the present inventor was that the circumstance of severe airway obstruction shown in FIG. 6C can occur in a small but significant percentage of patients with the PROSEAL laryngeal mask due to its larger enhanced cuff formation and due to presence of a drainage tube traveling through the distal cuff formation along the medial line.

The present inventor's first explanation for severe narrowing of the glottis was the large and noncompliant distal portion of the PROSEAL laryngeal mask cuff formation along the medial line and the presence of a stiff drain tube in this position. As in FIGS. 5B and 6C such thick distal cuff formation along the medial line can exert forces anteriorly on the cricoid and arytenoid cartilages and narrow the glottis in a small but significant percentage of patients when the distal cuff formation along the medial line was relatively too large for the dimensions of a patient's lower pharynx and esophageal inlet.

The present inventor's second explanation for severe narrowing of the glottis followed observations of depth of insertion of laryngeal masks; the depth of insertion of the PROSEAL laryngeal mask was not as deep compared to laryngeal mask designs with thin and compliant distal cuff formations along the medial line. The advantage of a greater depth of insertion, found in laryngeal mask designs with a thin and compliant distal cuff formation along the medial line, was that the arytenoid cartilages would be positioned within the recessed space of the bowl without mechanical forces exerted on their posterior aspect. With a shallower depth of insertion, often found with the PROSEAL laryngeal mask, the distal cuff formation would arrest immediately posterior to the arytenoid cartilages and exert substantial forces on their posterior surfaces, e.g. FIGS. 5B and 6C.

Figure 7:
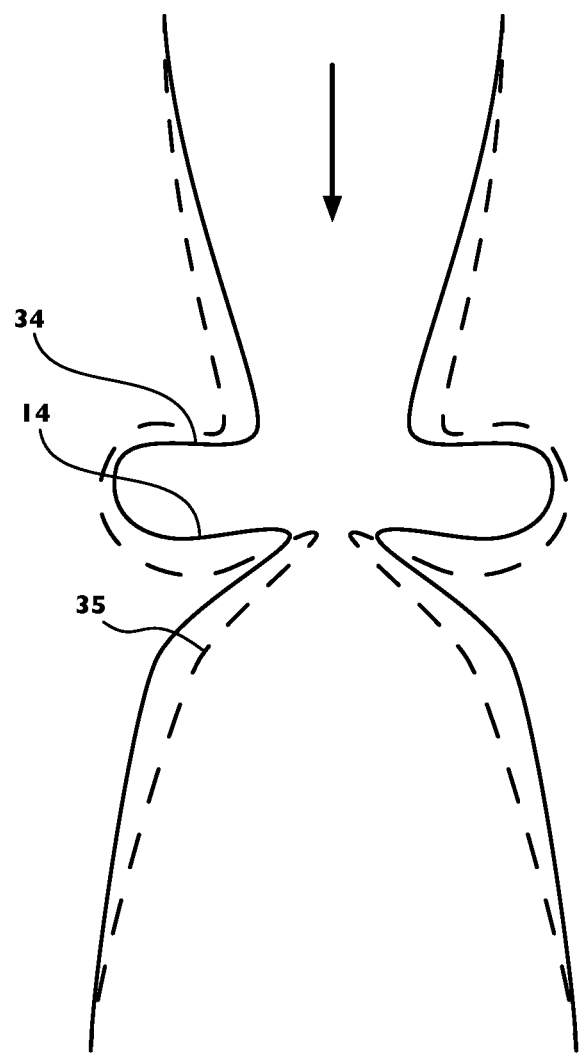
FIG. 7 is a view of laryngeal anatomy and is a coronal section through the vocal cords of the larynx at a location specified in FIG. 6B. The solid lines depict the position of the vocal cords with no gas flow. The dashed lines depict the position of the vocal cords with inspiratory gas flow.

The present inventor's third explanation for severe narrowing of the glottis accounted for effects of general anesthesia, where under the influence of general anesthesia the vocal cords behave as if they are paralyzed, and the influence of aerodynamic properties of the vocal cords; when oxygen and anesthetic gases flow from outside through the vocal cords and glottis into the lungs the vocal cords are pushed together because of the aerodynamic forces on their concave superior surfaces. FIG. 7 depicts a coronal section through the larynx and vocal cords at a section specified in FIG. 6B. The solid lines illustrate the position of the vocal cords 14 at rest when there is no gas flow into the lungs, and the dashed lines indicate the position of the vocal cords 14 when pushed together by inspiratory gas flow (indicated by the arrow).

The present inventor's conclusion from this observation-based discussion and the illustrations of FIGS. 5-7 was that the distal portion 84 of the cuff formation of a laryngeal mask 60 is one of the most critical aspects of construction, especially the distal cuff formation along the medial line as it is this portion of the cuff formation that enters the narrow space 37. If such distal portion along the medial line is large and noncompliant it may displace the larynx anteriorly and narrow the glottis; and the use of positive pressure ventilation during general anesthesia to overcome such airway obstruction will be of limited utility to improve such obstruction in lieu of the aerodynamic process illustrated in FIG. 7 impeding ingress of gases into the lungs.

Laryngeal masks 60, described herein, include a piriform-fossa conduit 92 to direct the insertion of orogastric tubes from outside the patient to the esophageal inlet completely within the interior of the piriform-fossa conduit 92 and with such orogastric tubes to suction liquid gastrointestinal contents from inside the esophagus or stomach or small intestines to the exterior of the patient and to thereby reduce the risk of pulmonary aspiration of liquid gastrointestinal contents. The laryngeal masks 60 with such a piriform-fossa conduit 92 can have a distal portion of the cuff formation along the medial line 136 that is thin and compliant and, by such a thin and compliant distal cuff formation along the medial line 136, can conform to the actual and potential space surrounding the circumference of the inlet to the larynx and avoid severe compression of the glottic opening 30.

Figure 8A:
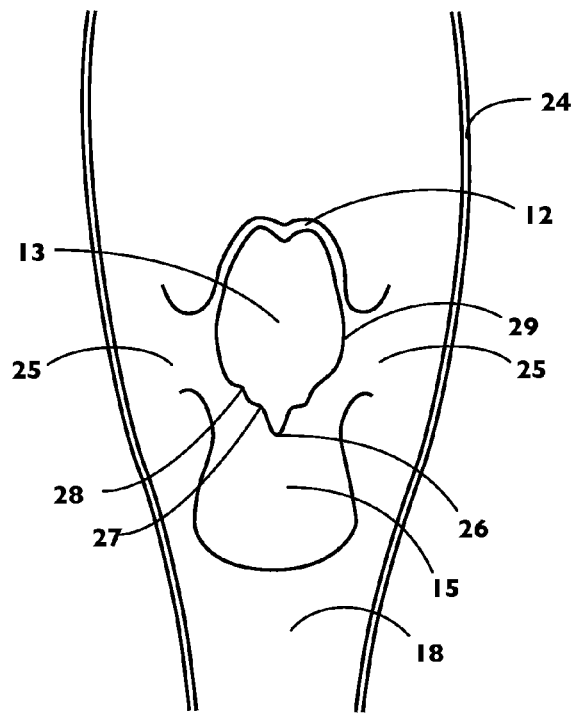
FIG. 8A is a view of pharyngeal anatomy and of structures of the anterior pharynx through a coronal section through the pharynx.

FIG. 8A is a view of pharyngeal anatomy and of structures of the anterior pharynx through a coronal section through the pharynx. The oval-shaped circumference of the laryngeal inlet 13 is defined by the epiglottis 12, aryepiglottic folds 29, cuneiform tubercle 28, arytenoid cartilage 27, and interarytenoid notch 26. On both sides of the laryngeal inlet are the piriform fossa 25 spaces bounded medially by aryepiglottic folds 29 and arytenoid cartilages 27 and laterally by the lateral pharyngeal wall 24. Inferior to the laryngeal inlet is the entrance to the esophagus 18 with an outline of the mucosal surface covering of the cricoid cartilage 15.

Figure 8B:
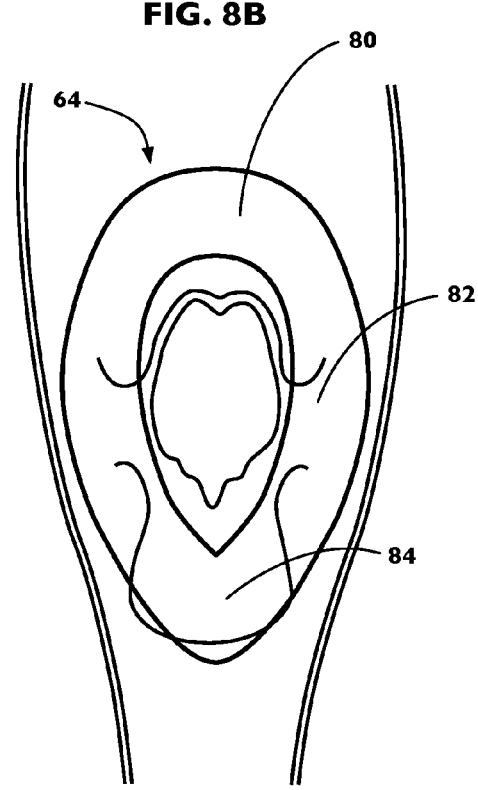
FIG. 8B depicts an outline of an inflatable cuff of a laryngeal mask correctly positioned in an unconscious patient superimposed on the anatomic illustration FIG. 8A.

FIG. 8B depicts an outline of an inflatable cuff 64 of a laryngeal mask correctly positioned in an unconscious patient superimposed on the anatomic illustration of FIG. 8A. The inflatable cuff 64 of the laryngeal mask conforms to the actual and potential space surrounding the circumference of the inlet to the larynx; and each portion of the inflatable cuff 64 has an anatomic correlate. The proximal portion 80 of the inflatable cuff 64 rests against the base of the tongue 11 (not shown). The lateral portions 82 of the inflatable cuff 64 occupy the piriform fossa 25. The distal portion 84 of the inflatable cuff 64 lies immediately posterior to the midline of the cricoid cartilage 15.

Figure 9A:
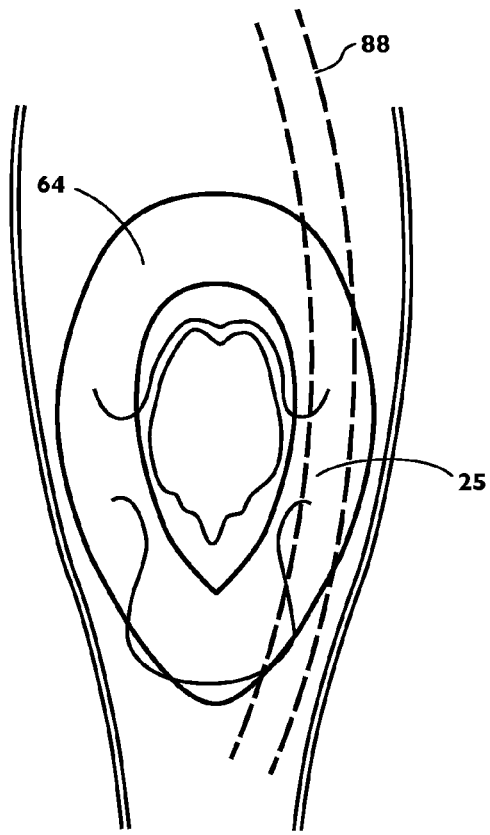
FIG. 9A depicts the anatomic illustration FIG. 8B and in dashed lines a conduit 88 traveling through the piriform fossa passing from the pharynx to the esophagus.

FIG. 9A depicts the illustration of FIG. 8B and, in dashed lines, a general conduit 88 starting in the pharynx and traveling through a piriform fossa passing to reach the esophagus; and FIG. 9A demonstrates how a conduit may take advantage of the natural anatomy of the pharynx to travel through a piriform fossa to reach the upper esophagus and thereby travel around the laryngeal inlet; such a route avoids passage directly posterior to the cricoid cartilage.

Figure 9B:
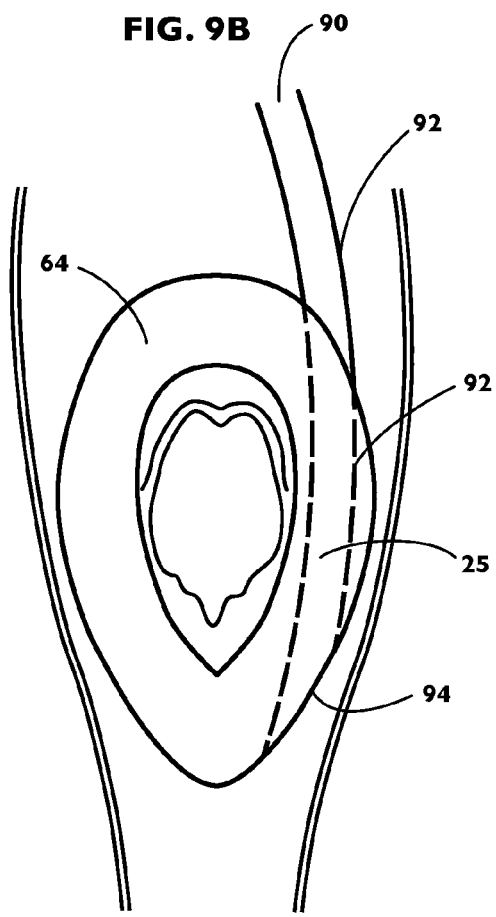
FIG. 9B depicts the anatomic illustration FIG. 9A and an outline of an embodiment of a laryngeal mask with a piriform-fossa conduit.

FIG. 9B further depicts the principles of an embodiment of a laryngeal mask with a piriform-fossa conduit 92; and the piriform fossa space 25 now accommodates both the inflatable cuff 64 and the presence of a segment of the piriform-fossa conduit 92. The walls of the piriform-fossa conduit 92 proximal to the mask portion are illustrated by the solid line, and the walls of the piriform-fossa conduit 92 in the cuff formation are illustrated by the dashed line. The piriform-fossa conduit 92 has a distal orifice 94 along an outer perimeter of the mask portion 61 and in the distal one-third of the mask portion 61, it does not intersect the medial line 136.

Figure 9C:
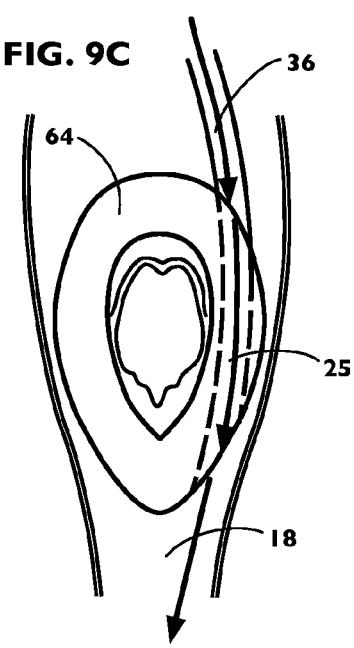
FIG. 9C illustrates the use of a piriform-fossa conduit to direct insertion of an orogastric tube from outside the patient to the esophageal inlet.

FIG. 9C depicts use of a piriform-fossa conduit 92 to direct insertion of an orogastric tube or medical instrument from outside the patient to the esophageal inlet. The top arrow illustrates passage through the pharynx; the middle arrow illustrates passage around the circumference of the inlet to the larynx and through a piriform fossa to reach the esophageal inlet; and the bottom arrow illustrates passage beyond the laryngeal mask further into the esophagus.

Figure 10:
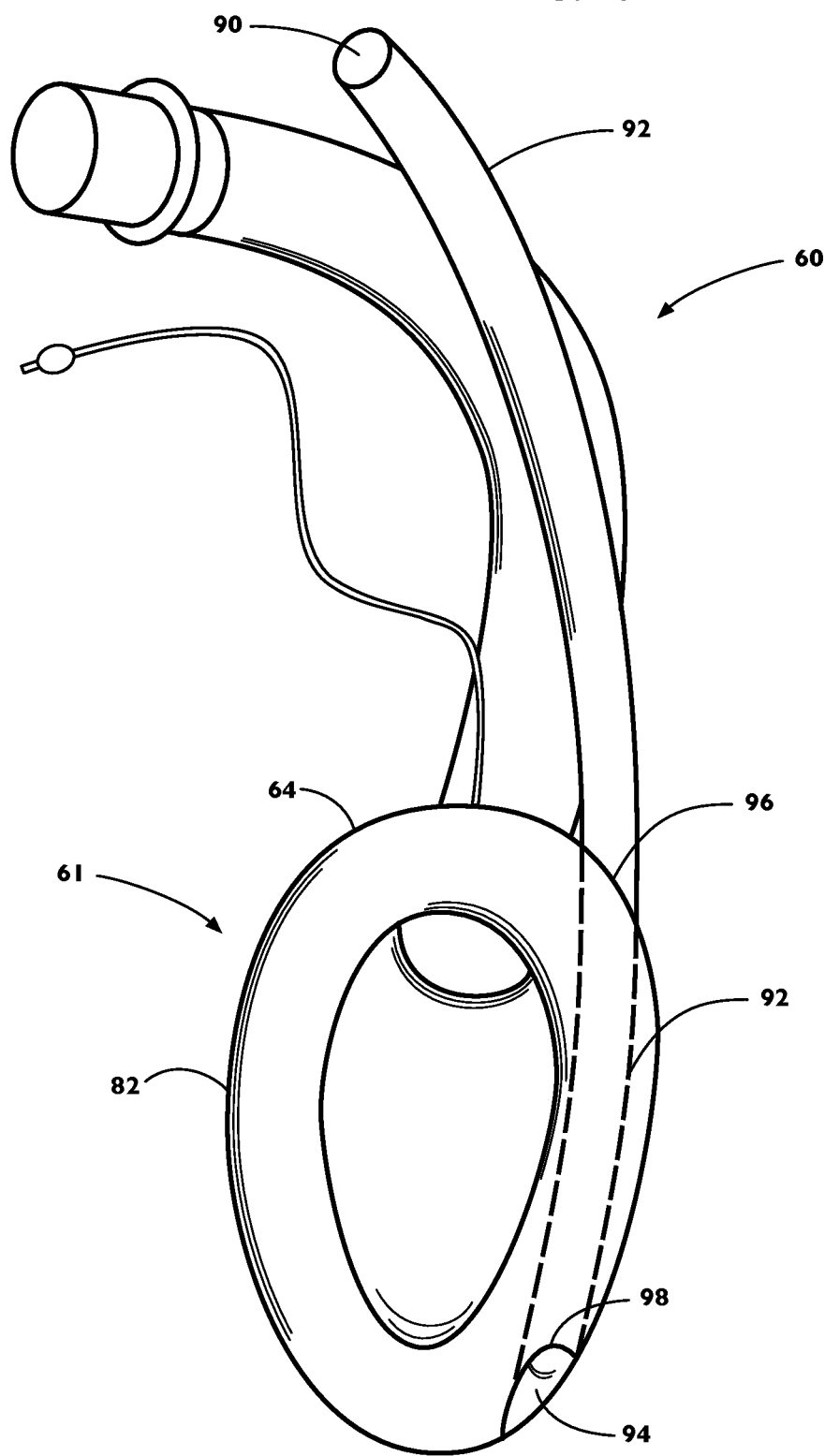
FIG. 10 is a perspective view of an embodiment of a laryngeal mask with a piriform-fossa conduit in a laryngeal mask that also has an inflatable cuff element in the cuff formation.

FIG. 10 is a perspective view of an embodiment of a laryngeal mask with a piriform-fossa conduit 92 in a laryngeal mask 60 that also has an inflatable cuff 64 in the cuff formation. The piriform-fossa conduit 92 travels through the lateral portion 82 of the cuff 64; and the piriform-fossa conduit 92 has a sealed entrance 96 with the inflatable cuff 64 and a sealed exit 98 with the inflatable cuff 64 to preserve inflation integrity of the inflatable cuff 64. The distal orifice 94 of the piriform-fossa conduit 92 is along an outer perimeter of the cuff 64 proximate the distal end of the mask but avoiding the medial line 136 through the distal portion of the cuff formation.

These components may be formed of a soft and flexible medically approved biocompatible polymeric material, such as soft and flexible polyvinyl chloride (PVC) or silicone rubber, or other harder and less flexible medically approved biocompatible polymeric materials, including adhesives.

The typical dimensions of the mask portion 61 of an adult laryngeal mask 60 are approximately as follows: the length 126 of the mask portion 61 of an adult laryngeal mask 60 is 9 cm to 10 cm. The width of the mask portion 61 of an adult laryngeal mask 60 is 5 cm to 6 cm. The lateral portions 82 of the cuff formation are approximately 10 mm to 15 mm wide. By comparison, the width of an orogastric tube of size 14 Fr is 4.6 mm. An adequate size piriform-fossa conduit 92 for passage of such size 14 Fr orogastric tube is comparable to a size 26 Fr soft PVC nasopharyngeal airway. The inner diameter of a soft PVC 26 Fr nasopharyngeal airway is 6.5 mm and the outer diameter is 8.7 mm and the thickness of the wall of such nasopharyngeal airway is 1.1 mm. A piriform-fossa conduit 92 of adequate dimension for passage of a size 14 Fr orogastric tube may constitute an element of the cuff formation of an adult laryngeal mask 60 without exceeding the typical dimensions in such masks. Although the piriform-fossa conduit 92 is made from soft and flexible material, it has sufficient structural integrity to maintain a passageway under 60 cm $H_2O$ pressure, as is typical of cuff inflation pressure.

Figure 11:
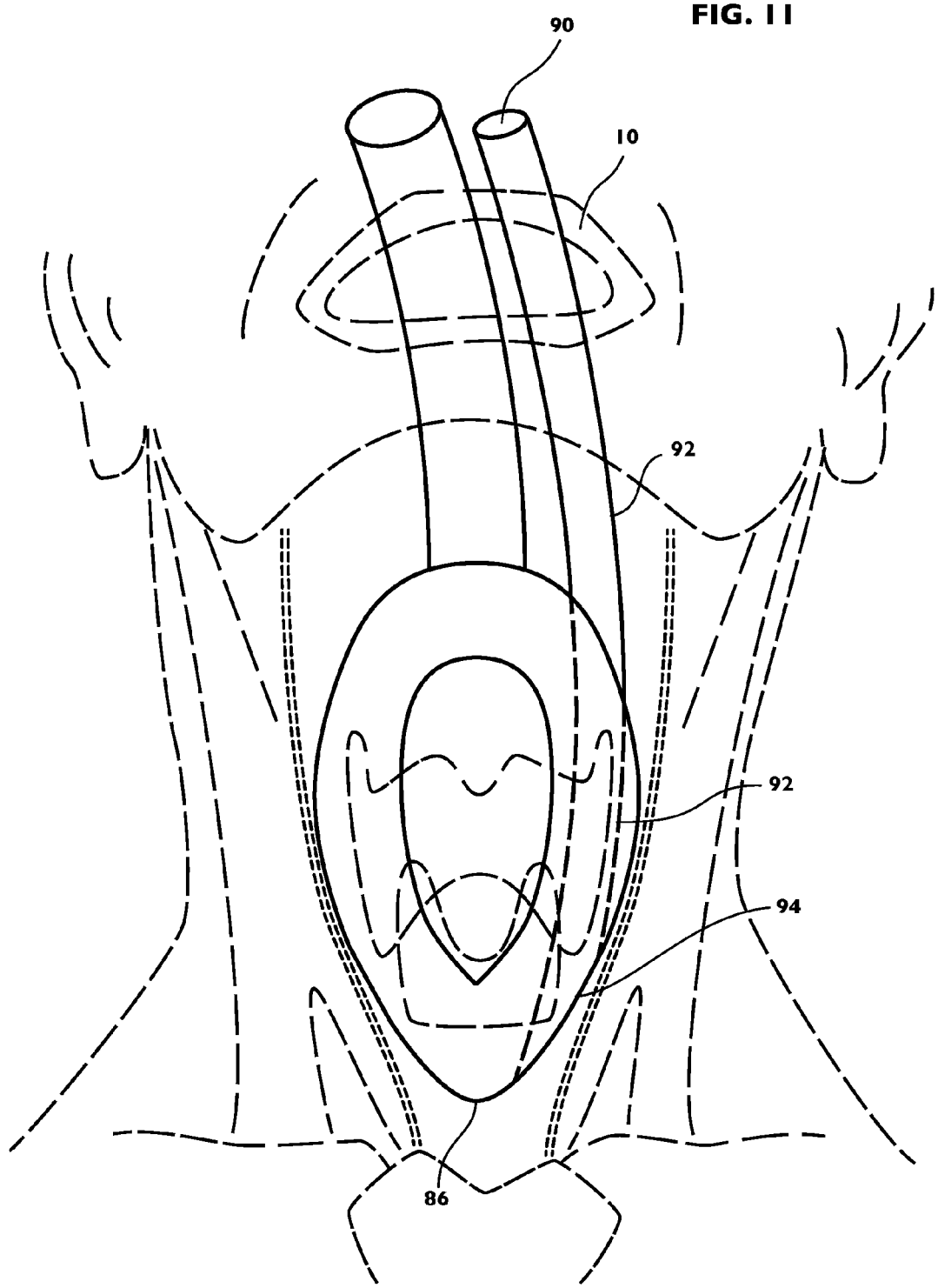
FIG. 11 is a front view of head and neck anatomy shown by dashed lines and an outline of an embodiment of a laryngeal mask with a piriform-fossa conduit in a correct anatomic position.

FIG. 11 is a front view of head and neck anatomy shown by dashed lines and an outline of an embodiment of a laryngeal mask with a piriform-fossa conduit 92 in a correct anatomic position. The proximal orifice 90 of the piriform-fossa conduit 92 is outside the mouth 10, and its distal orifice 94 is along an outer perimeter of the cuff formation and is located within the upper esophagus. The piriform-fossa conduit 92 is illustrated by dashed line as an element of the cuff formation. The distal orifice avoids the medial line 136 in the distal cuff formation and the midline distal point 86.

Figure 12:
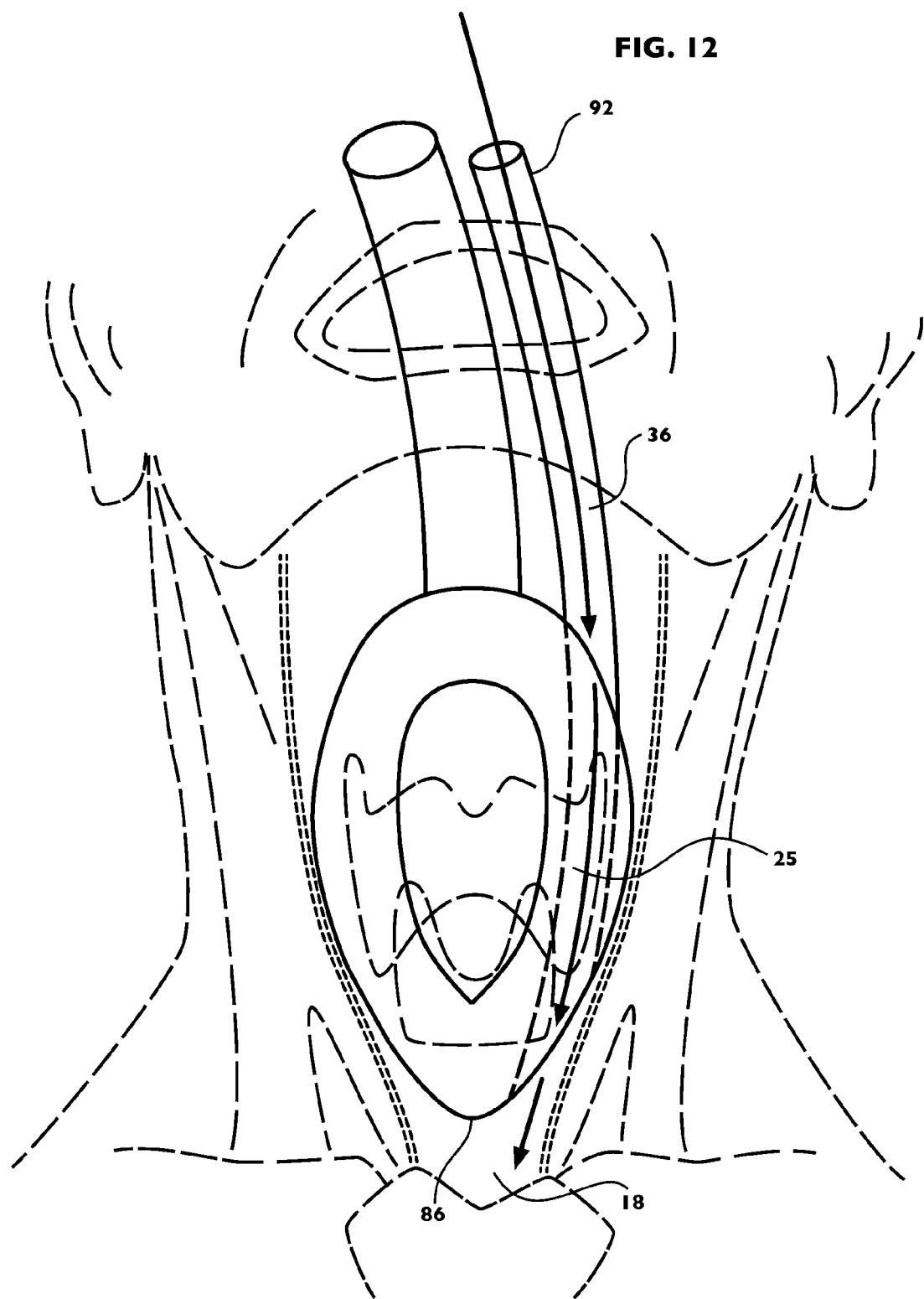
FIG. 12 shows the use of a piriform-fossa conduit to direct insertion of an orogastric tube from outside the patient to the esophageal inlet.

FIG. 12 depicts use of the piriform-fossa conduit 92 to direct insertion of an orogastric tube or medical instrument from outside the patient to the esophageal inlet. The top arrow illustrates passage through the pharynx 36; the middle arrow illustrates passage around the circumference of the laryngeal inlet and through the piriform fossa 25 to reach the esophageal inlet; and the bottom arrow illustrates passage beyond the laryngeal mask further into the esophagus 18.

Figure 13:
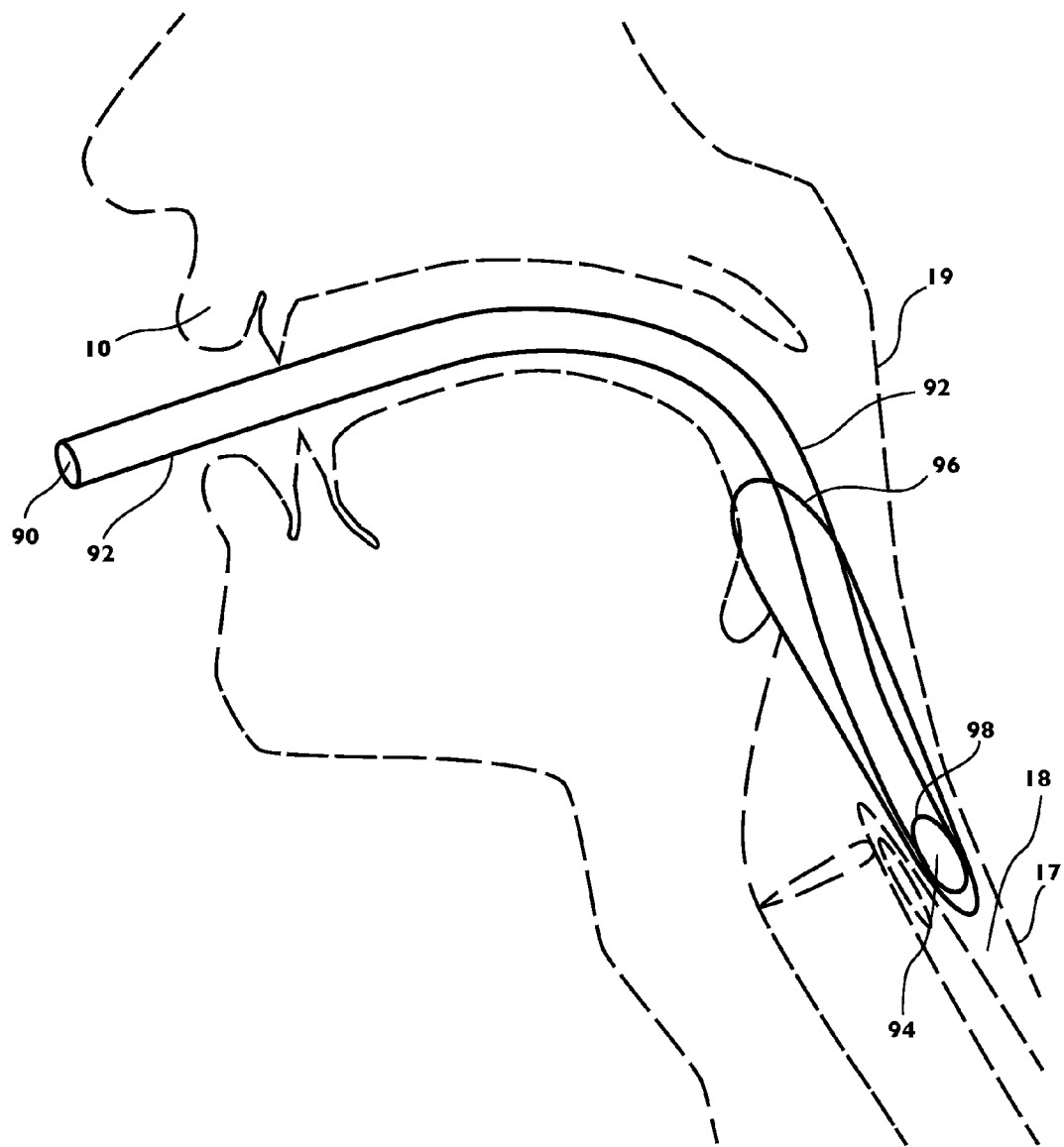
FIG. 13 is a side view of the anatomy of the pharynx shown by dashed lines and an outline of an embodiment of a laryngeal mask with a piriform-fossa conduit in correct anatomic position.
Figure 14:
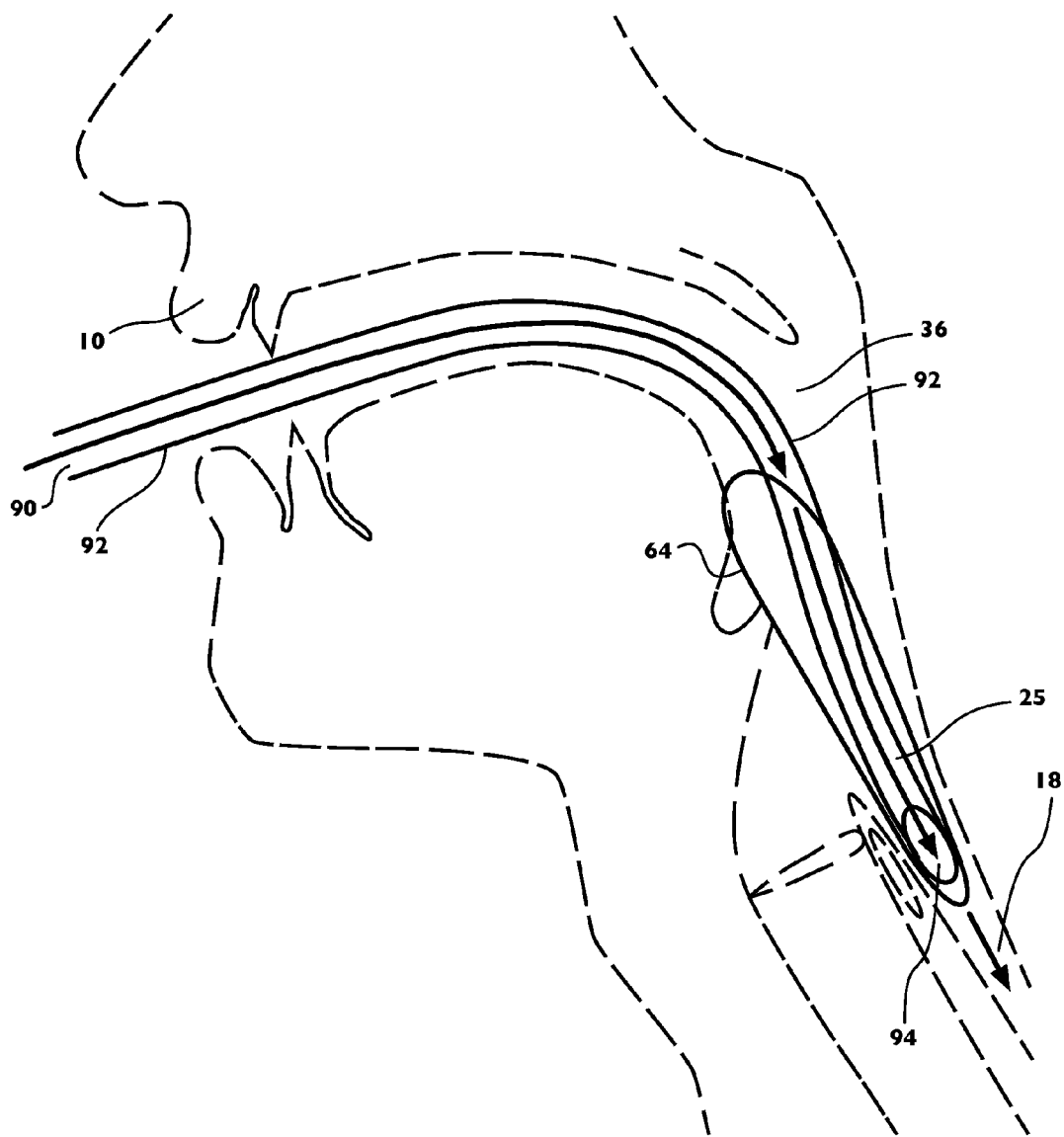
FIG. 14 shows the use of a piriform-fossa conduit to direct insertion of an orogastric tube from outside the patient to the esophageal inlet.

FIG. 13 depicts a side view of the anatomy of the pharynx shown by dashed lines and an outline of an embodiment of a laryngeal mask with a piriform-fossa conduit 92 in correct anatomic position. The proximal orifice 90 of the piriform-fossa conduit 92 is outside the mouth 10, and its distal orifice 94 is within the upper esophagus. The piriform-fossa conduit 92 is illustrated as an element of the lateral portion of the cuff formation. FIG. 14 depicts use of the piriform-fossa conduit 92 to direct insertion of an orogastric tube or medical instrument, as shown in FIG. 12, but from a side view.

Figure 15:
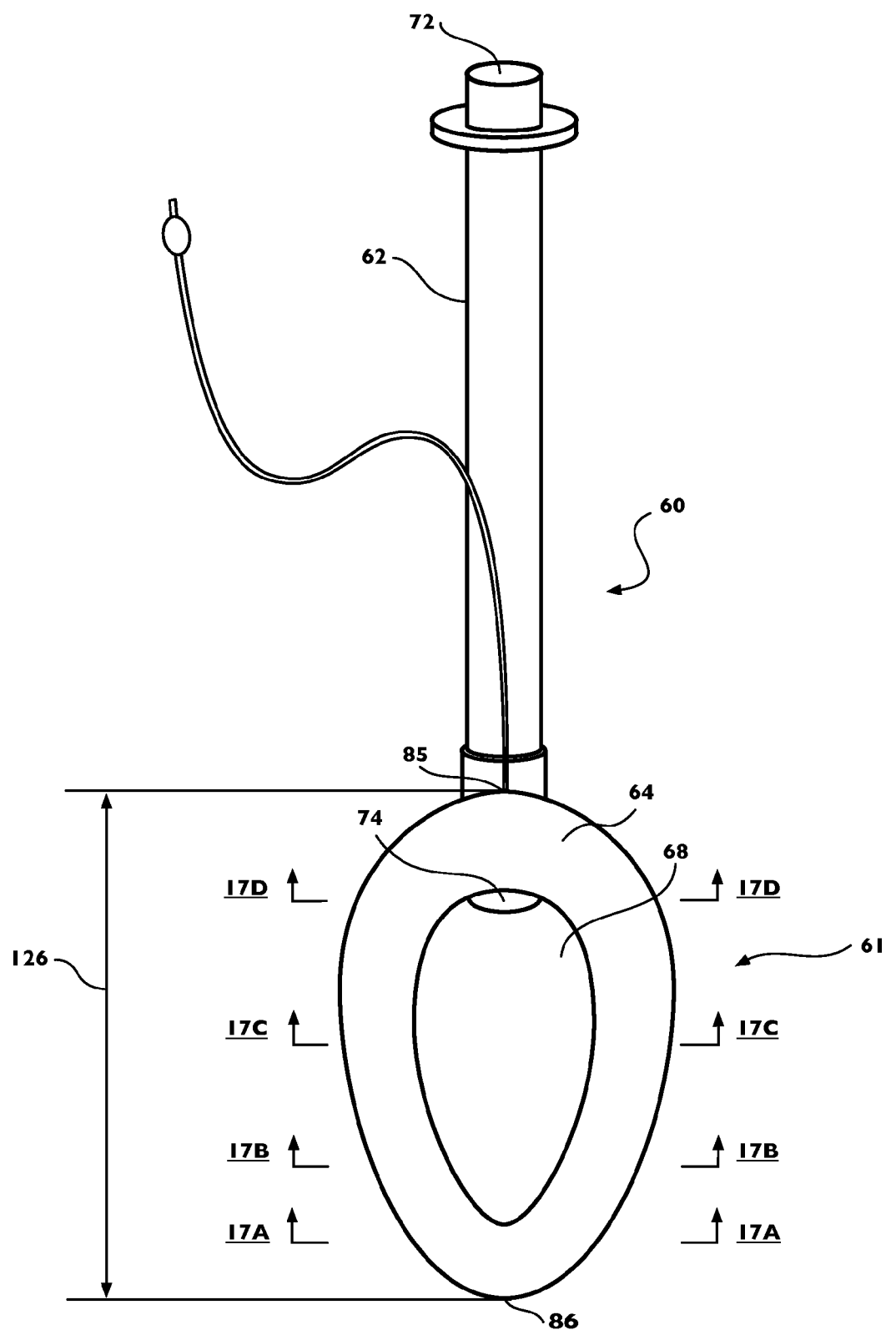
FIG. 15 illustrates a laryngeal mask depicted in front view, specifying four sections.
Figure 16:
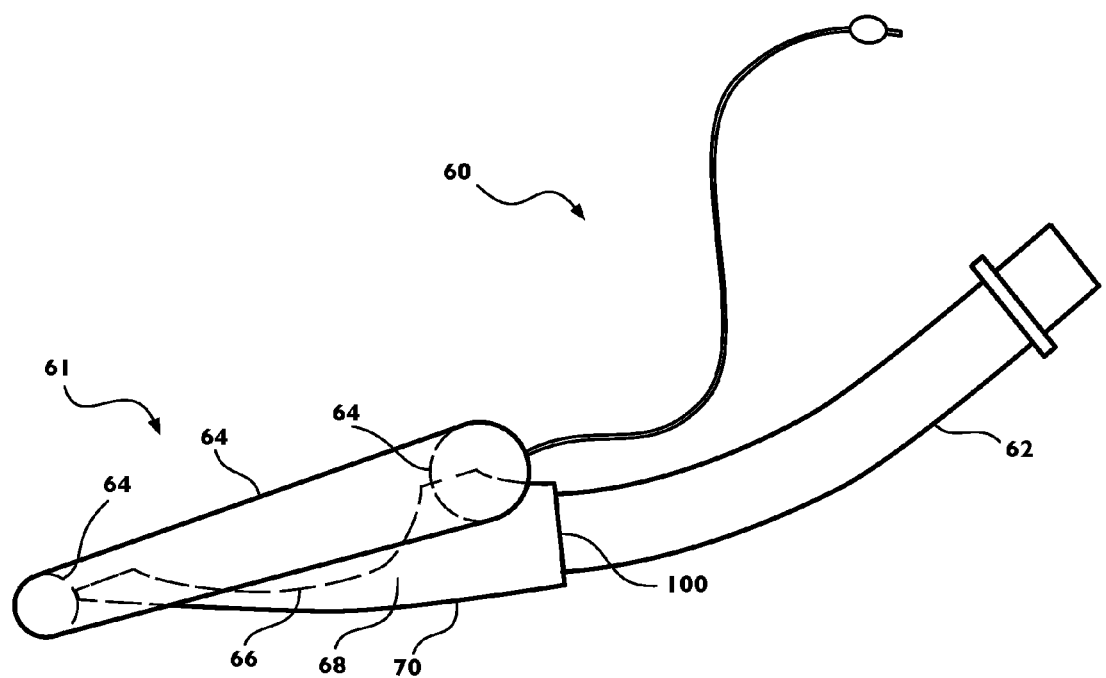
FIG. 16 illustrates a laryngeal mask depicted in side view.

FIG. 15 illustrates a laryngeal mask 60 in front view, specifying four sections, and FIG. 16 illustrates the same laryngeal mask 60 in side view. The laryngeal mask 60 includes an airway tube 62 with a proximal orifice 72 and a mask portion 61 with an inflatable cuff 64 attached to a perimeter of a bowl structure 68 and establishing an oval space that is recessed and concave in the forward-facing direction and that also includes an aperture 74 in fluid communication with the airway tube 62. The bowl structure 68 has a posterior surface 70 and is joined to the airway tube 62 at junction 100.

Figure 17D:
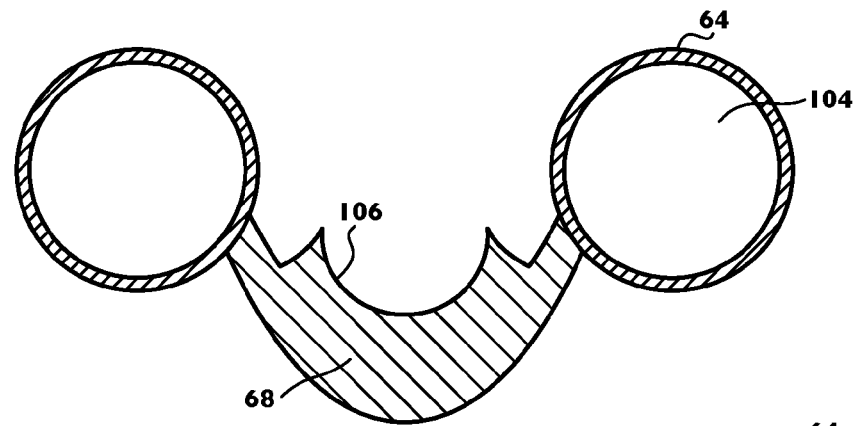
FIGS. 17A-D depict four sections through the laryngeal mask at the sectional indications of FIG. 15.
Figure 17C:
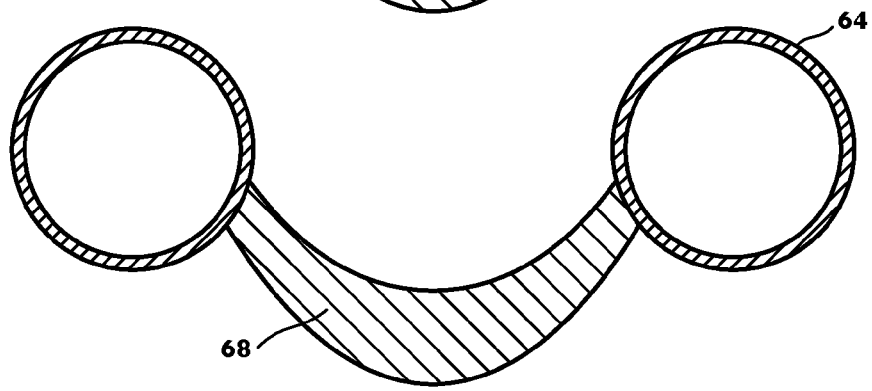

There are four sections indicated in FIG. 15, and the section labeled 17C (wherein the sectional view is shown in FIG. 17C) is located at the middle position of the length 126 of the mask portion 61; the section is midway between the most proximal point 85 of the cuff formation and most distal point 86 of the cuff formation.

FIGS. 17A-D depict four sections (with corresponding reference numbers) through the mask portion 61 of the laryngeal mask 60, as specified in FIG. 15.

Figure 17B:
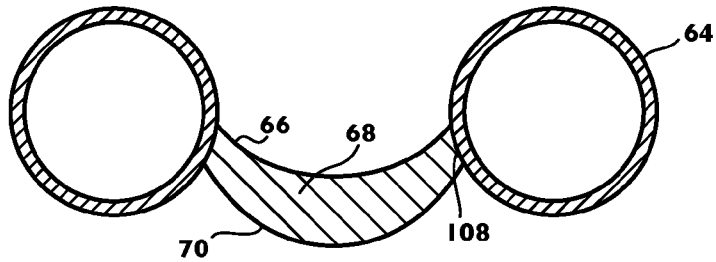
Figure 17A:
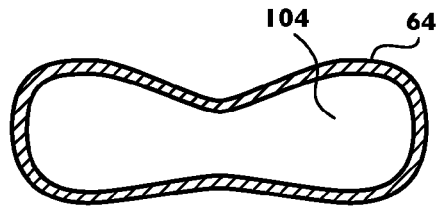

FIG. 17A is a section distal to the interior space of the recessed bowl of the mask 60 and through the distal portion 84 of the cuff formation showing the substance of the cuff material 64 and the air or other fluid 104 filling the cuff 64; the air or other fluid 104 can be pumped into the cuff 64 via an inflation line 76 and a pilot balloon/one-way valve 78 communicating with the interior of the inflatable cuff 64.

FIG. 17B is a section through the interior of the recessed bowl structure 68 in the distal one-half of the mask portion; the bowl structure 68 has an anterior surface 66 and a posterior surface 70. The bowl structure 68 and inflatable cuff 64 are joined at junction 108.

FIG. 17C is a section through the mask portion 61 that divides the mask portion 61 into proximal half 140 and distal half 142 of equal lengths 130.

FIG. 17D is a section through the interior of the recessed bowl in the proximal one-half of the mask portion 61; the anterior surface 66 of the bowl structure 68 has a concave arc 106 for the aperture 74 of the airway tube.

Figure 18D:
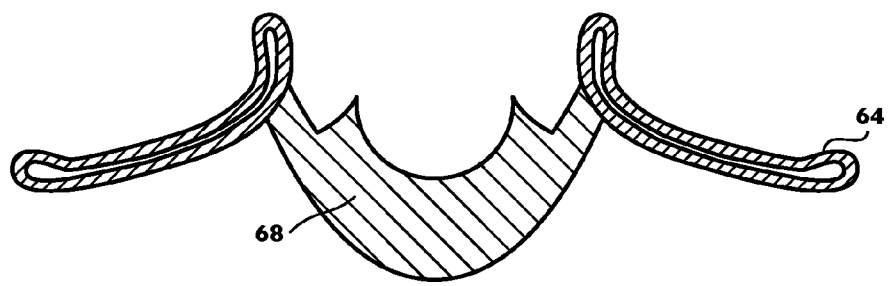
FIGS. 18A-D depict the four sections of FIGS. 17A-D with the inflatable cuff in the deflated state.
Figure 18C:
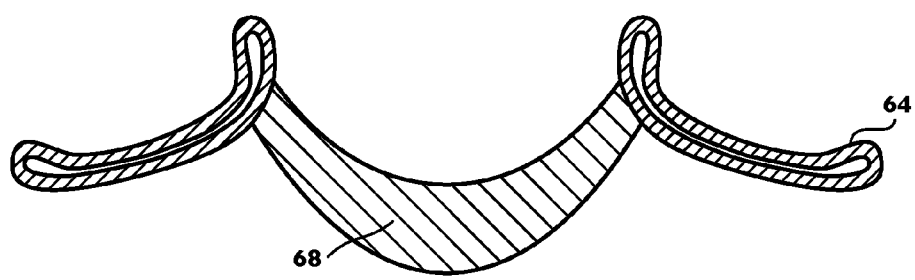
Figure 18B:
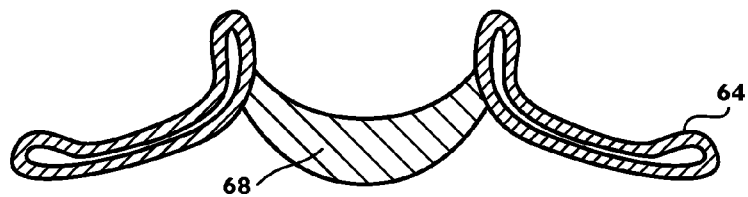
Figure 18A:
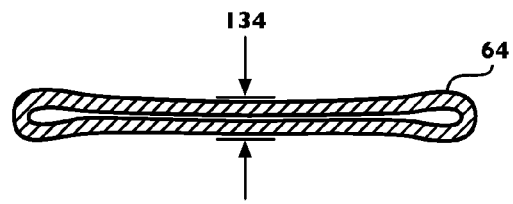

FIGS. 18A-D correspond respectively to FIGS. 17A-D when the inflatable cuff 64 of the cuff formation is in a deflated state. FIG. 18A shows that, in such deflated state, the thickness 134 of the distal cuff formation along the medial line is very thin and comprises just the opposed anterior and posterior walls of the inflatable cuff 64. Such thin and compliant deflated tip with thickness 134 is adapted to enter posterior to the larynx into the thin space 37 of FIG. 5A.

Figure 19A:
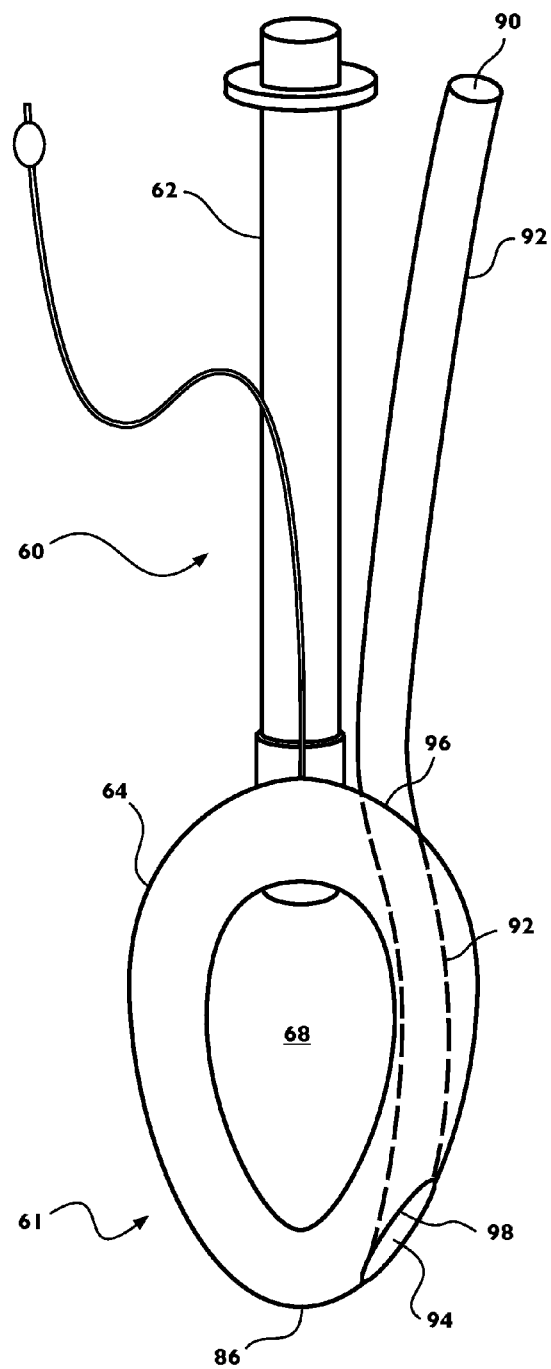
FIG. 19A-B illustrate an embodiment of a laryngeal mask with a piriform-fossa conduit depicted in front view.

FIG. 19A illustrates an embodiment of a laryngeal mask 60 with a piriform-fossa conduit 92 depicted in front view. The laryngeal mask 60 includes an airway tube 62 with a proximal orifice 72 and a mask portion 61 with an inflatable cuff 64 attached to a perimeter of a bowl structure 68 and establishing an oval space that is recessed and concave in the forward-facing direction and that also includes an aperture 74 in fluid communication with the airway tube 62. The piriform-fossa conduit 92 is an element of the cuff formation; and the piriform-fossa conduit travels along the length of the laryngeal mask with proximal orifice 90 proximate the proximal orifice 72 of the airway conduit 62 and distal orifice 94 along the outer perimeter of the cuff formation proximate the distal end of the cuff formation. In FIG. 19A, the segment of piriform-fossa conduit 92 that is part of the cuff formation is drawn in dashed line. The piriform-fossa conduit 92 travels through the lateral portion of the cuff formation and around the oval space that is recessed and concave in the forward-facing direction.

Figure 19B:
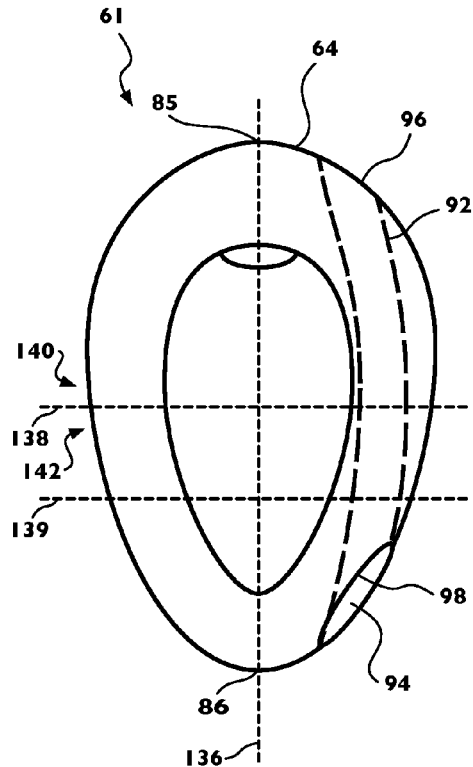

FIG. 19B depicts the mask portion 61 of the embodiment of laryngeal mask with piriform-fossa conduit 92 of FIG. 19A. The midway dividing line 138 demarcates the distal one-half of the mask portion 61, and the line 139 demarcates the distal one-third of the mask portion; and in the distal one-half of the mask portion the piriform-fossa conduit 92 travels only in the cuff formation; and the distal orifice 94 is along an outer perimeter of the cuff formation in the distal one-third of the mask portion 61.

Figure 20:
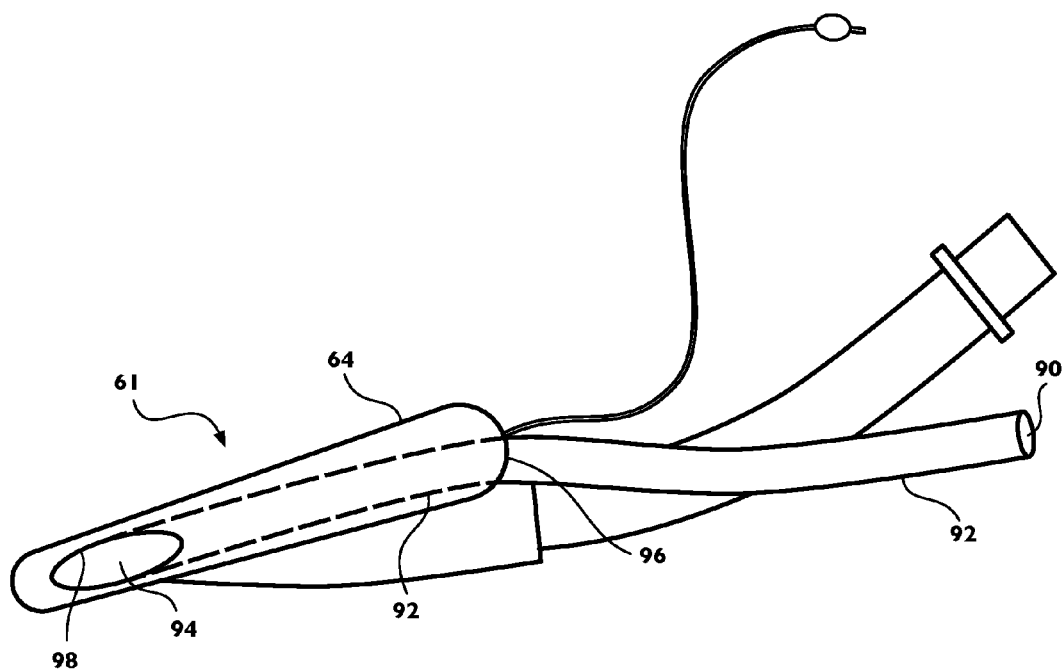
FIG. 20 illustrates an embodiment of a laryngeal mask with a piriform-fossa conduit depicted in side view.

FIG. 20 is a side view of the embodiment of the laryngeal mask with piriform-fossa conduit of FIGS. 19A-B.

In FIG. 19A and in FIG. 20, the piriform-fossa conduit 92 enters the cuff formation with a sealed entry 96 that preserves the integrity of the inflatable cuff 64; and the piriform-fossa conduit 92 exits cuff formation with a sealed exit 98 that preserves the inflation integrity of the inflatable cuff 64; and the interior of the piriform-fossa conduit 92 is not in fluid communication with the interior of the inflatable cuff 64.

Figure 21:
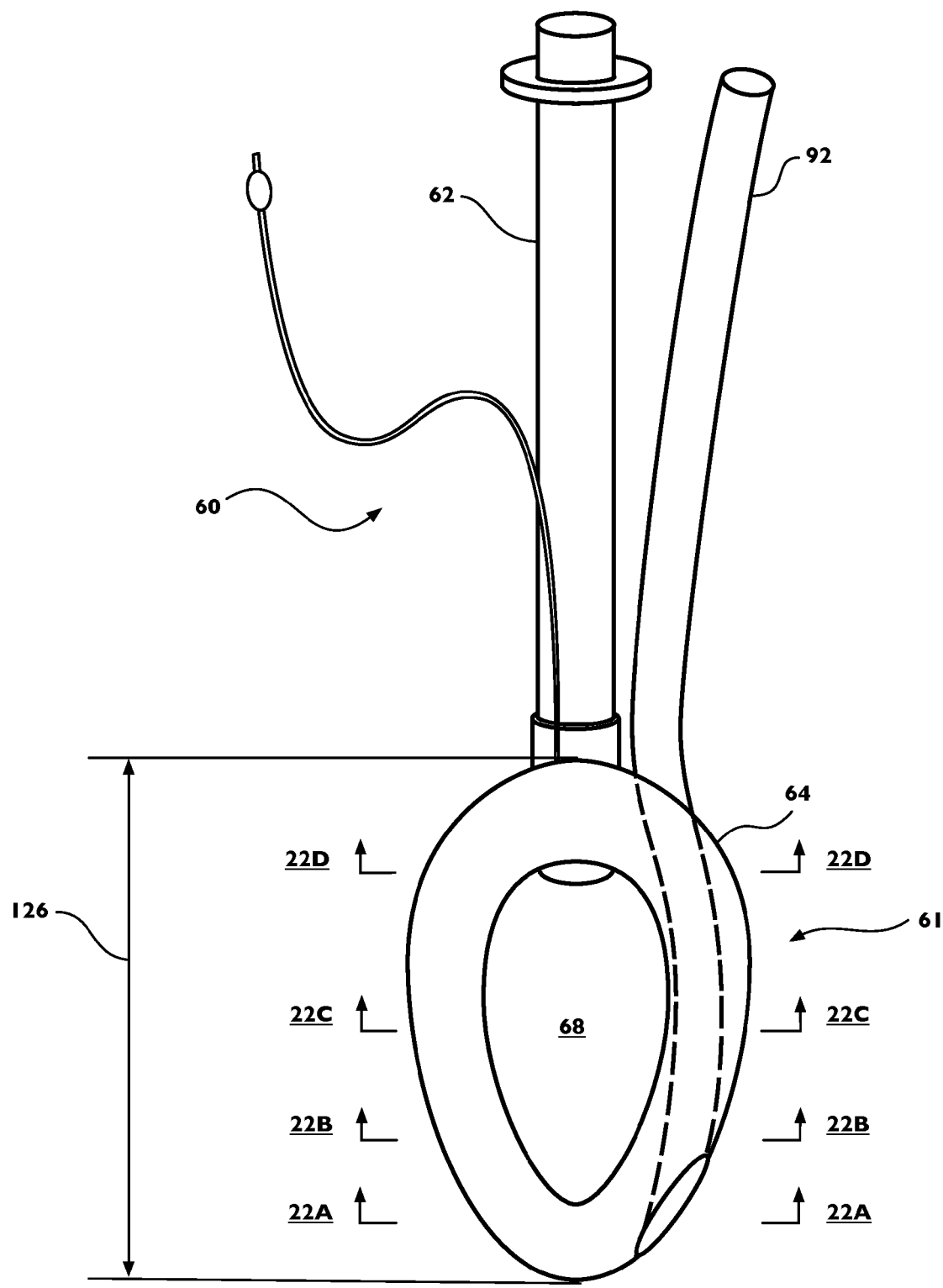
FIG. 21 depicts an embodiment of a laryngeal mask with a piriform-fossa conduit, specifying four sections.

FIG. 21 depicts an embodiment of a laryngeal mask 60 with a piriform-fossa conduit 92 and specifies four sections. The section labeled 22C (wherein the sectional view is shown in FIG. 22C) is located at the middle position of the length 126 of the mask portion 61; the section is midway between the most proximal point 85 of the cuff formation and most distal point 86 of the cuff formation.

FIGS. 22A-D depict four sections (with corresponding reference numbers) through the mask portion 61 of the laryngeal mask 60, as specified in FIG. 21.

Figure 22D:
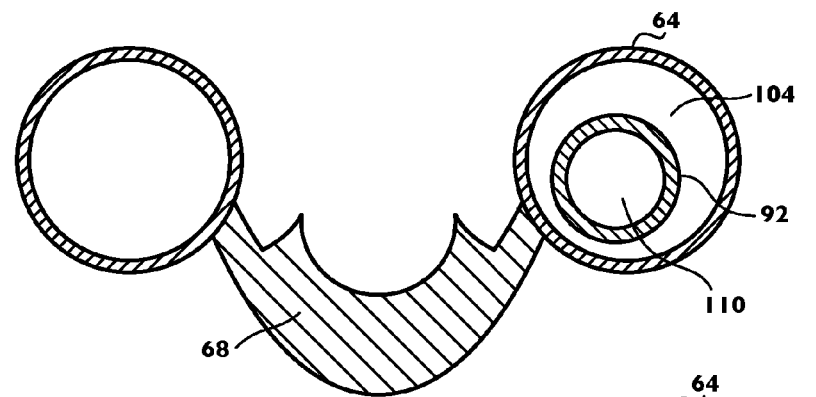
FIGS. 22A-D depict four sections through the laryngeal mask with a piriform-fossa conduit at the sectional indications of FIG. 21.
Figure 22C:
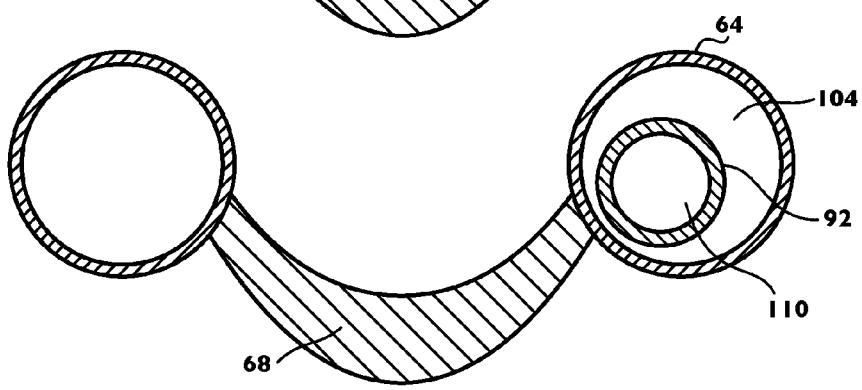
Figure 22B:
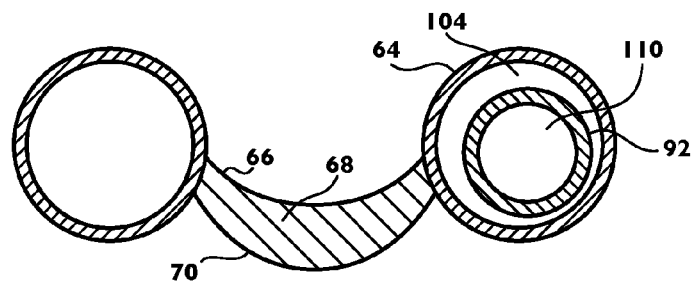
Figure 22A:
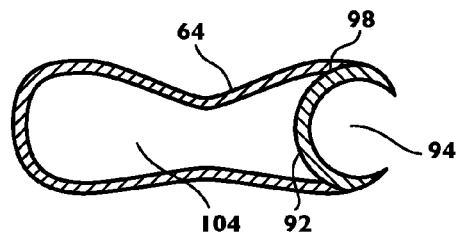

FIG. 22A is a section distal to the interior space of the recessed bowl of the mask 60 and through the distal portion 84 of the cuff formation and depicts the inflatable cuff material 64, air or other fluid 104 filling the inflatable cuff 64, an arc section through the distal orifice 94 of the piriform-fossa conduit 92, the distal orifice 94 of the piriform-fossa conduit 92 along the outer perimeter of the cuff formation, the distal orifice 94 of the piriform-fossa conduit opening to an exterior environment outside the laryngeal mask, and the sealed exit 98 of the piriform-fossa conduit 92 with the inflatable cuff 64. The cuff formation at the section FIG. 22A includes both the inflatable cuff 64 and the piriform-fossa conduit 92.

FIG. 22B is a section through the interior of the recessed bowl in the distal one-half of the mask portion 61; the bowl structure 68 has an anterior surface 66 and a posterior surface 70. The cuff formation includes inflatable cuff material 64 and air or other fluid 104 filling the inflatable cuff 64; and in the interior of the inflatable cuff 64 is the piriform-fossa conduit 92 and the interior or lumen 110 of the piriform-fossa conduit 92. The cuff formation at the section FIG. 22B includes both inflatable cuff 64 and piriform-fossa conduit 92.

FIG. 22C is a section through the mask portion 61 and divides the mask portion 61 into proximal half 140 and distal half 142 of equal lengths 130. The cuff formation at the section FIG. 22C includes both inflatable cuff 64 and piriform-fossa conduit 92.

FIG. 22D is a section through the interior of the recessed bowl in the proximal one-half of the mask portion 61; the anterior surface 66 of the bowl structure 68 has a concave arc 106 for the aperture 74 of the airway tube. In the embodiment of a laryngeal mask 60 with a piriform-fossa conduit 92 of FIGS. 19A-B and FIG. 20, the piriform-fossa conduit 92 lies entirely within the interior of an inflatable cuff 64 at this proximal location. The cuff formation at the section FIG. 22D includes both the inflatable cuff 64 and the piriform-fossa conduit 92.

Figure 23D:
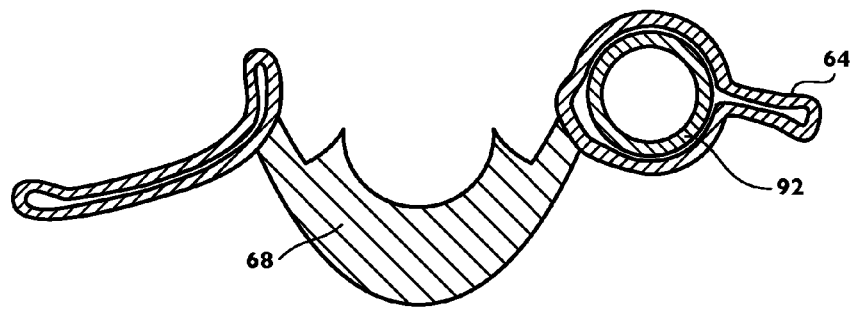
FIGS. 23A-D depict the four sections of FIGS. 22A-D with the inflatable cuff in the deflated state.
Figure 23C:
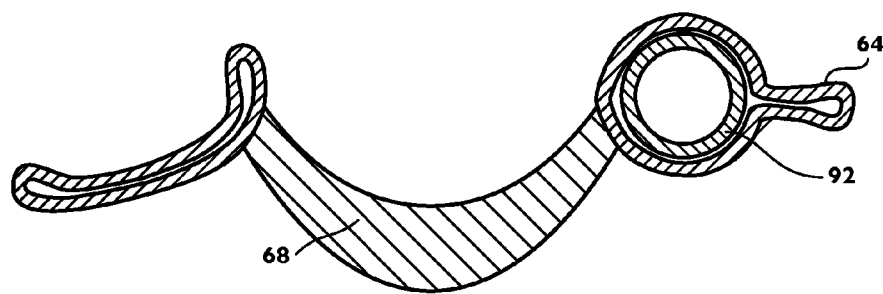
Figure 23B:
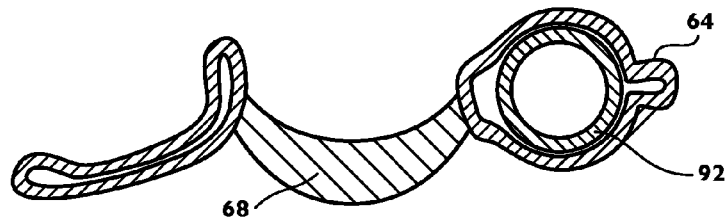
Figure 23A:
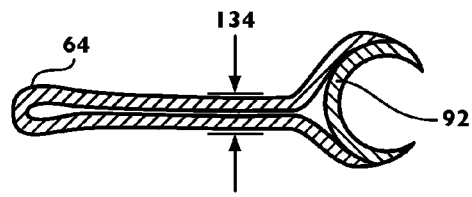

FIGS. 23A-D correspond respectively to FIGS. 22A-D when the inflatable cuff 64 of the cuff formation is in a deflated state. FIG. 23A shows that, in such deflated state, the thickness 134 of the distal cuff formation along the medial line is very thin and comprises just the opposed anterior and posterior walls of the inflatable cuff. Such a thin and compliant deflated tip with thickness 134 is adapted to enter posterior to the larynx into the thin space 37 of FIG. 5A.

FIG. 23A demonstrates that in an embodiment of the laryngeal mask with a piriform-fossa conduit, the thickness 134 of the distal cuff formation 84 along the medial line 136 may be identical to the thickness 134 in the distal cuff formation 84 along the medial line 136 in an embodiment of laryngeal mask that does not have a piriform-fossa conduit. Because the piriform-fossa conduit 92 travels within the lateral portion 82 of the cuff formation the laryngeal mask 60 with piriform-fossa conduit 92 can have a distal cuff formation along the medial line 136 that is thin and compliant and that conforms to the actual and potential space surrounding the circumference of the inlet to the larynx.

Further, the distal cuff formation 84 along the medial line 136 can also be more pliable/flexible (due at least in part to the absence of a conduit) than lateral portions 82 of the cuff formation through or along which the piriform-fossa conduit 92 passes. Such a thin distal portion 84 of the cuff formation along the medial line 136, as shown in FIG. 23A, allows the laryngeal mask 60 to pass posterior to the larynx into the esophageal inlet without distorting the laryngeal inlet.

By illustration of one of many possible embodiments, FIGS. 24A-D depict four sections, corresponding respectively to FIGS. 17A-D and FIGS. 22A-D, through a mask portion 61 of a laryngeal mask 60 with a piriform-fossa conduit 92. In FIGS. 24A-D, the piriform-fossa conduit 92 may be manufactured in part with the bowl structure 68 of the mask portion 61; and in FIGS. 24A-D the piriform-fossa conduit does not travel strictly within the interior of an inflatable cuff 64 in the lateral portion 82 of the cuff formation.

Figure 24D:
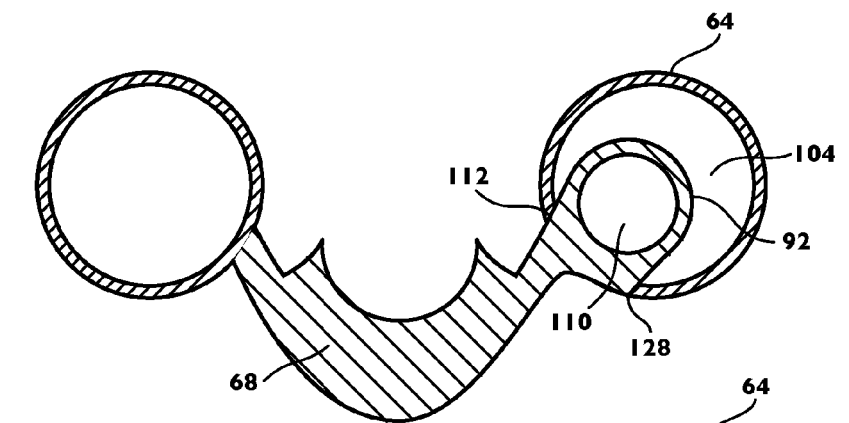
FIGS. 24A-D depict four sections through a different manufacturing embodiment of a laryngeal mask with a piriform-fossa conduit.
Figure 24C:
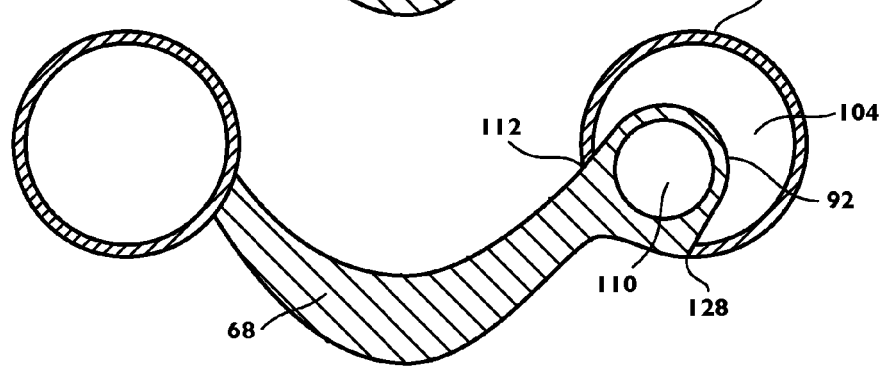
Figure 24B:
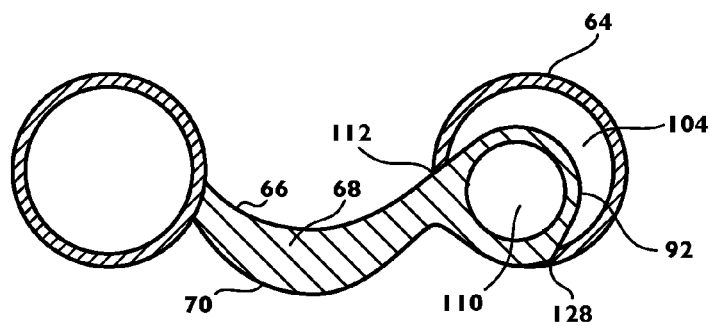
Figure 24A:
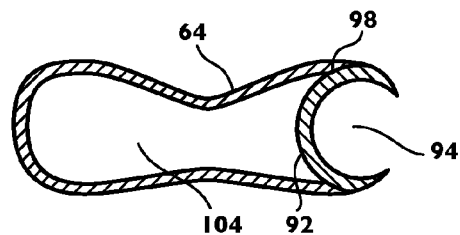

FIGS. 24B-D are sections through the interior of the recessed bowl of the mask portion 61; the bowl structure 68 has an anterior surface 66 and a posterior surface 70. The cuff formation includes inflatable cuff material 64 and air or other fluid 104 filling the inflatable cuff 64; within the cuff formation and adjacent to the inflatable cuff 64 is the piriform-fossa conduit 92 and the interior or lumen 110 of the piriform-fossa conduit 92. The cuff formation at section FIG. 24A-D includes both the inflatable cuff 64 and the piriform-fossa conduit 92. The inflatable cuff 64 element of the cuff formation is joined to the bowl formation 68 and piriform-fossa conduit 92 at an anterior juncture 112 and the inflatable cuff 64 element of the cuff formation is joined to the bowl formation and piriform-fossa conduit at a posterior juncture 128.

By illustration of this embodiment in FIGS. 24A-D of a laryngeal mask 60 with a piriform-fossa conduit 92, the piriform-fossa conduit 92 and inflatable cuff 64 are both part of the lateral portion 82 of the cuff formation; and, in the cuff formation, it is not necessary for the piriform-fossa conduit 92 to be completely surrounded by the air or fluid filling the inflatable cuff 64; and, in a cuff formation, the piriform-fossa conduit 92 may not travel strictly within the interior of an inflatable cuff 64.

Also by illustration of this embodiment of FIGS. 24A-D of a laryngeal mask 60 with a piriform-fossa conduit 92, such laryngeal mask 60 can be manufactured in a variety of embodiments by those skilled in the art of manufacture of artificial airway devices; and the piriform-fossa conduit 92 may be formed of a soft and flexible medically approved biocompatible polymeric material, such as soft and flexible polyvinyl chloride (PVC) or silicone rubber, or other harder and less flexible medically approved biocompatible polymeric materials, including adhesives. The piriform-fossa conduit 92 need not be made of a single segment of material; and the piriform-fossa conduit may be formed joining several segments of conduit together. The piriform-fossa conduit 92 does not need to have a circular cross section; and the piriform-fossa conduit does not require a cross-sectional profile that is constant throughout its length.

Figure 25:
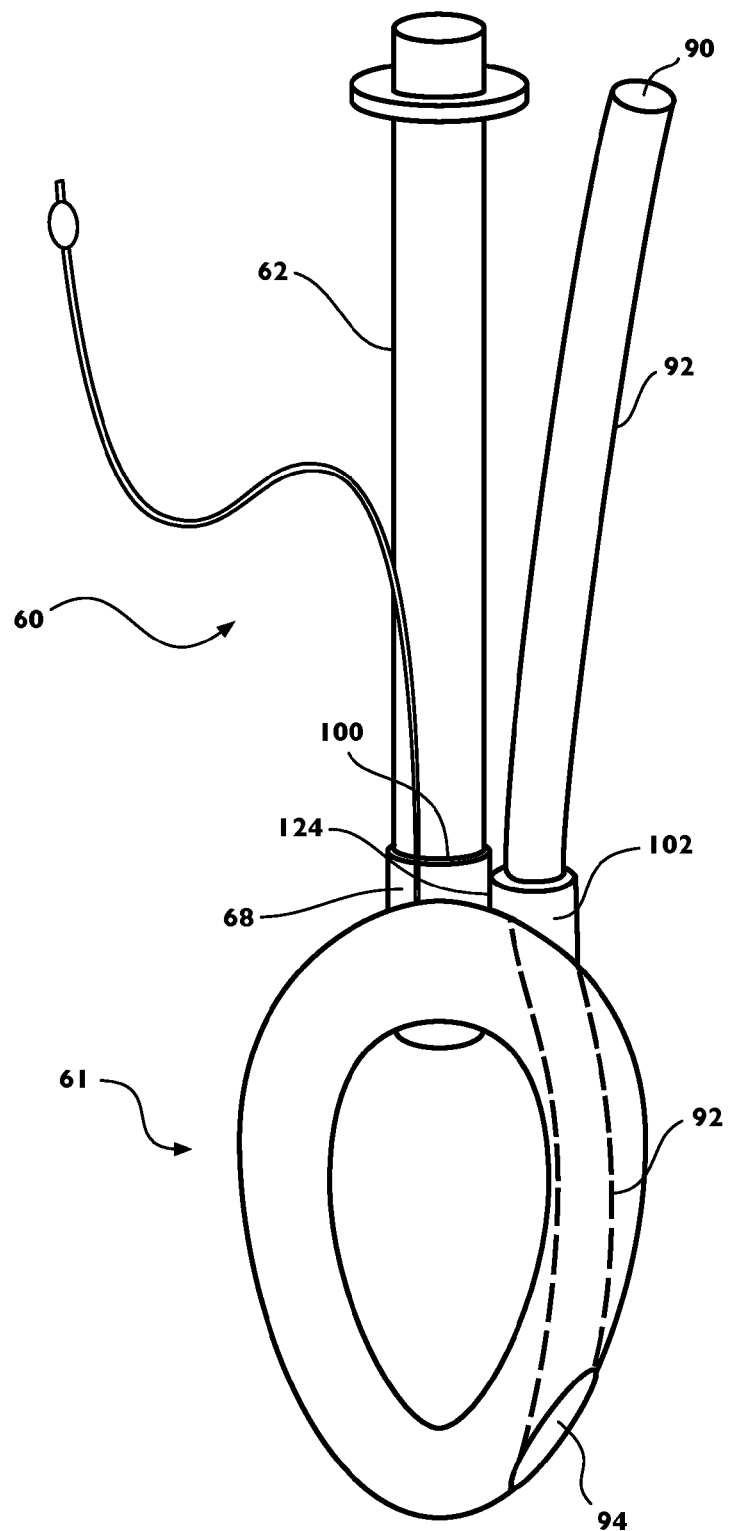
FIG. 25 is a front view of a laryngeal mask with a piriform-fossa conduit with a mount coupling.
Figure 26:
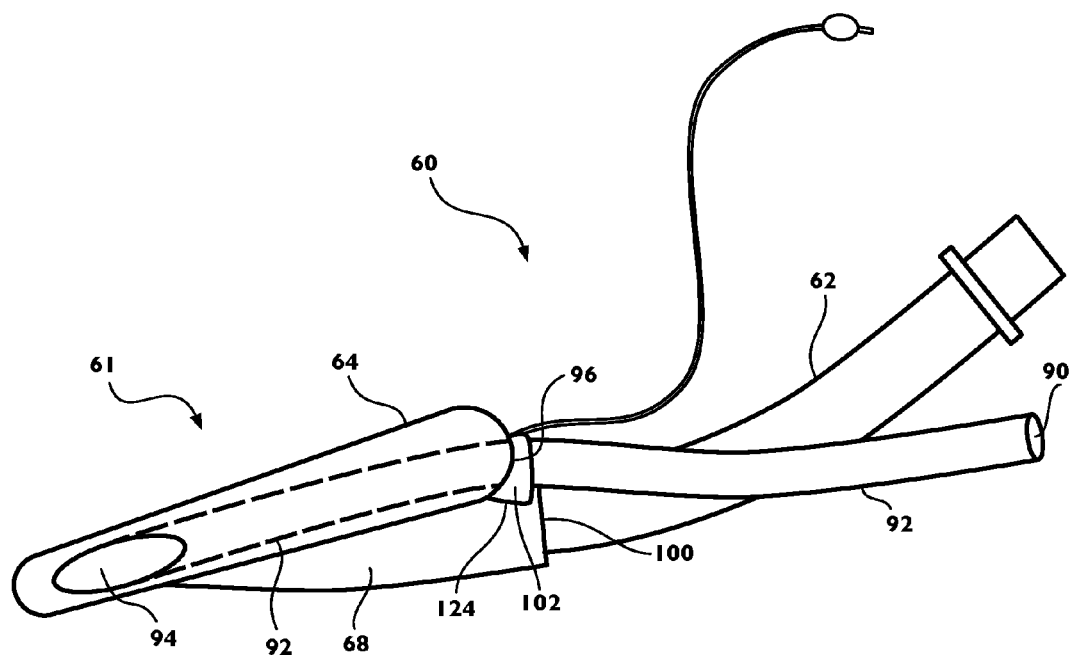
FIG. 26 is a side view of a laryngeal mask with a piriform-fossa conduit with a mount coupling.

FIG. 25 is a front view of one of many possible embodiments of a laryngeal mask 60 with a piriform-fossa conduit 92 with a mount coupling 102. FIG. 26 is a side view of the same embodiment. The mount coupling 102 is located proximate the proximal end of the mask portion 61 and proximate the sealed entrance 96 with the inflatable cuff 64. The mount coupling 102 surrounds the outside of the piriform-fossa conduit 92 and can provide mechanical stability for the piriform-fossa conduit 92 near the proximal end of the mask portion 61, especially if the mount coupling 102 is bonded to the bowl structure 68 at junction 124. The mount coupling 102 may be manufactured as part of the bowl structure 68. An advantage of the mount coupling 102 is that two segments of piriform-fossa conduit 92 may be joined in airtight manner preserving a lumen of the conduit 92; and the two segments of piriform-fossa conduit 92 may have different mechanical properties. The conduit within the cuff formation may be formed of soft and flexible material, and the conduit not part of the cuff formation may be formed of harder and less flexible material. Specifically, the segment of piriform-fossa conduit 92 emerging from the patient's mouth may be stiffer to facilitate insertion of orogastric tubes or medical instruments.

Figure 27A:
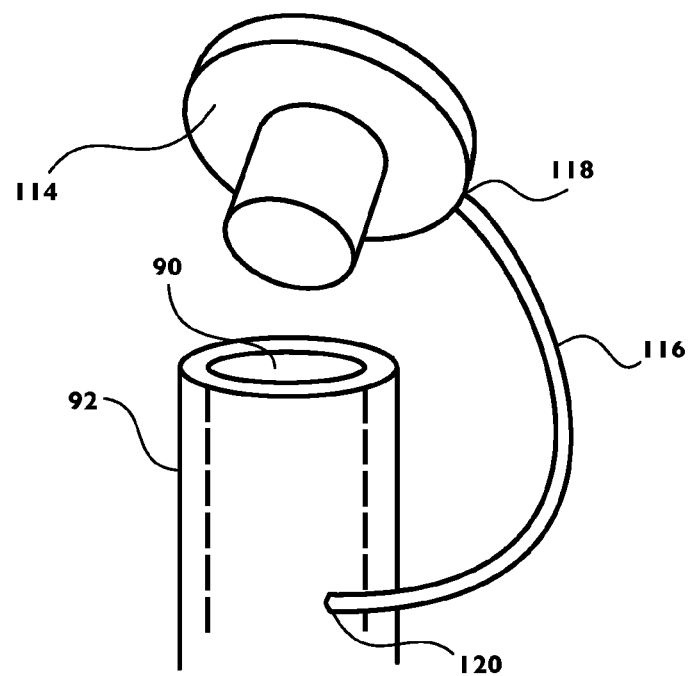
FIGS. 27A-C show a plug structure for a piriform-fossa conduit and front views of a plug removed from and inserted into the proximal orifice of the piriform-fossa conduit.

FIG. 27A is a perspective view of a plug structure 114 for a piriform-fossa conduit 92 that can be inserted and removed from the proximal orifice 90 of the piriform-fossa conduit 92. There is an attachment length 116 that attaches the plug structure 114 to the outside of the piriform-fossa conduit 92. The attachment length 116 is bonded to the plug structure 114 at junction 118 and is bonded to the outside of the piriform-fossa conduit 92 at junction 120. An advantage of such attachment length 116 is to prevent the plug structure 114 from entering into the proximal orifice 72 of the airway tube 62.

Figure 27B:
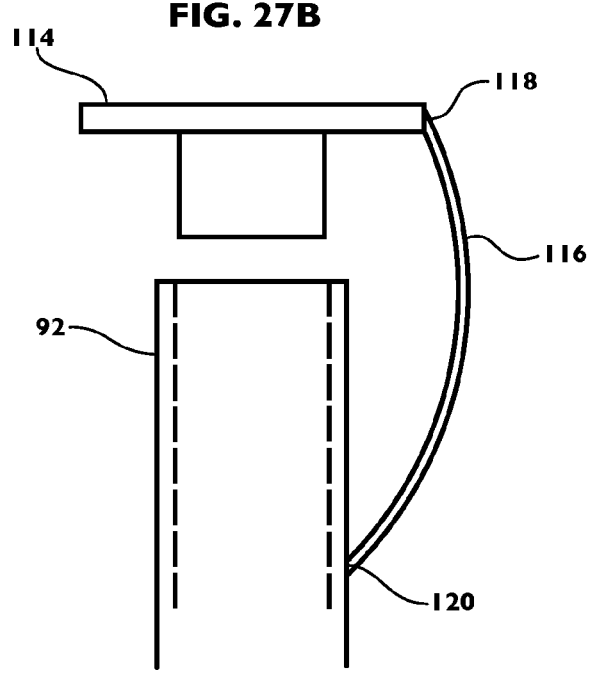
Figure 27C:
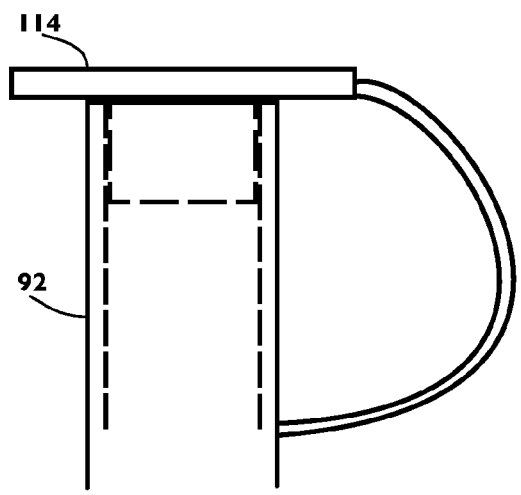

FIG. 27B is a front view of the plug structure 114 removed from the proximal orifice 90 of the piriform-fossa conduit 92. FIG. 27C is a front view of the plug structure 114 inserted into the proximal orifice 90 of the piriform-fossa conduit 92.

An advantage of the plug structure 114 is to prevent venting of respiratory and anesthetic gases from the pharynx to the exterior of the patient. Such a process would occur during positive pressure ventilation when pressurized gases in the patient's pharynx entered the distal orifice 94 and then travel via the lumen 110 of the piriform-fossa conduit 92 and escape to outside the patient through the proximal orifice 90. By occluding the proximal orifice 90 the plug structure 114 prevents this process. The plug structure 114 may be reversibly removed from the proximal orifice 90 to permit insertion of an orogastric tube or medical instrument into the lumen 110 of the piriform-fossa conduit 92.

Figure 28:
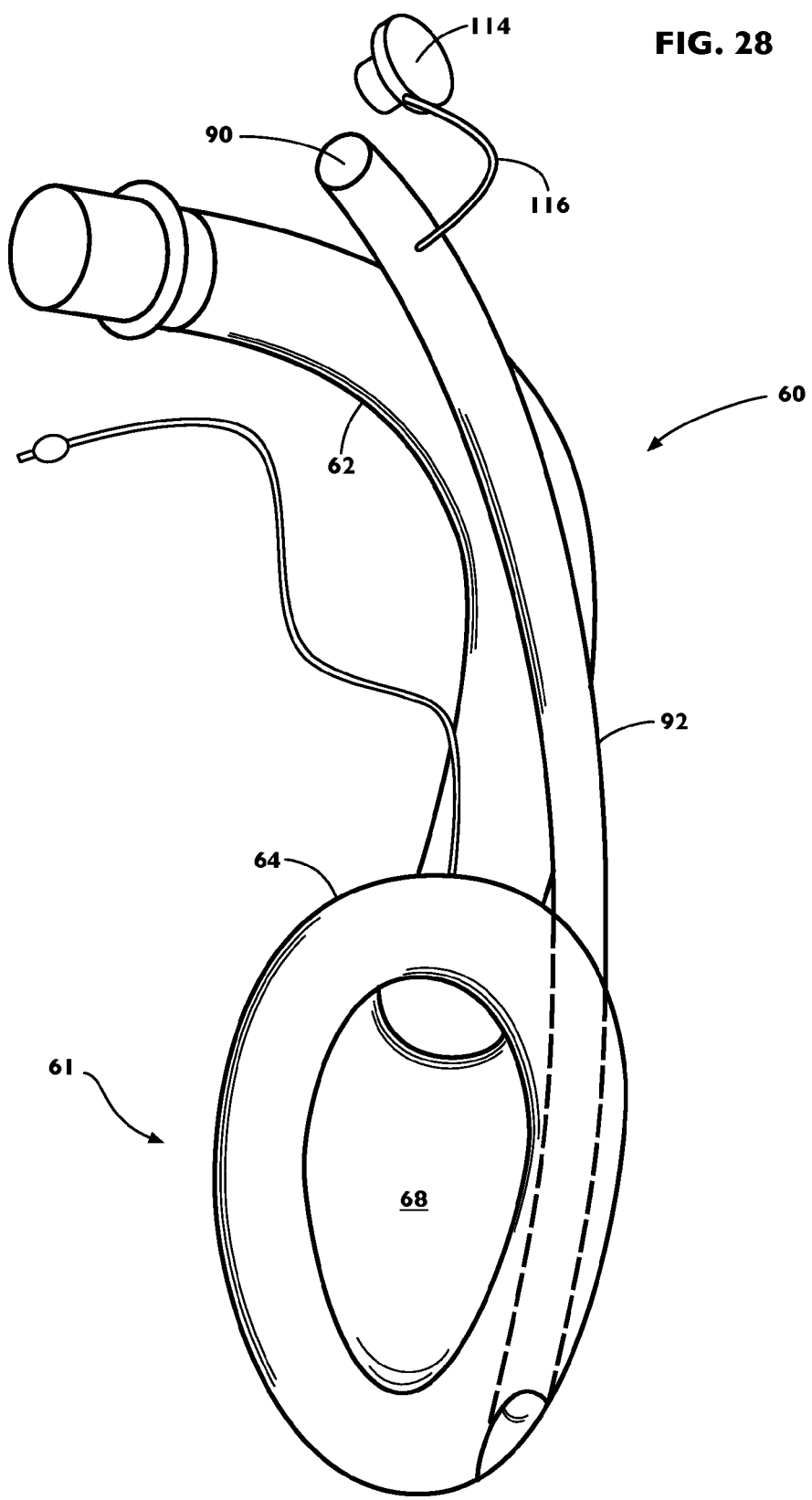
FIG. 28 is a perspective view of an embodiment of a laryngeal mask with a piriform-fossa conduit with a plug structure bonded by an attachment length near the proximal orifice of the piriform-fossa conduit.

FIG. 28 is a perspective view of an embodiment of a laryngeal mask 60 with a piriform-fossa conduit 92 and a plug structure 114 bonded by an attachment length 116 to the outside of the piriform-fossa conduit near the proximal orifice 90.

Those skilled in the art of manufacture of artificial airway devices may form a laryngeal mask 60 with a piriform-fossa conduit 92 from medically approved polymeric materials, using processing, forming, assembling, joining, and sterilization processes. Artificial airway devices can be so manufactured by a variety of processes with considerations of expense and ease or complexity of assembly. The laryngeal masks 60 can be formed of a soft and flexible medically approved polymeric material, such as soft and flexible polyvinyl chloride (PVC), silicone rubber, or other harder and less flexible medically approved biocompatible polymeric materials, including adhesives. Mask components can be formed and shaped by a variety of production processes, including but not limited to molding methods (e.g., blow molding, extrusion molding, injection molding, rotational molding), casting methods (e.g., dip casting), thermoforming, stamping methods, three-dimensional printing, etc.; and components can be joined by a variety of methods including but not limited to welding methods (e.g., by heat, pressure, vibration, ultrasound), adhesive bonding methods (e.g., mechanical adhesion, chemical adhesion), mechanical fastening methods, friction fitting methods, etc.

The material characteristics of the piriform-fossa conduit 92 that constitutes an element of the cuff formation can be of a soft and flexible material (e.g., silicone rubber, soft polyvinyl chloride (PVC)) and, by such a choice of material, several advantages can be gained. By such choice of soft and flexible material for the piriform-fossa conduit 92, it would be easier to introduce the laryngeal mask 60 into the mouth and pharynx; by such choice of soft and flexible material, the piriform-fossa conduit 92 would be less likely to cause traumatic insertion of the laryngeal mask 60, injury, discomfort, or sore throat; by such choice of soft and flexible material, the piriform-fossa conduit 92 would be less likely to cause injury to nerves of the tongue, pharynx, and larynx; by such choice of soft and flexible material, the piriform-fossa conduit 92 would be less likely to cause mucosal injury if the mask portion 61 would remain positioned with a patient's pharynx for an extended period of time.

If the piriform-fossa conduit 92 is formed of material that is excessively thin or flexible, it might collapse when exposed to the inflation pressure, 60 cm $H_2O$, commonly used in an inflatable cuff 64 element of a cuff formation. A suitable conduit for the piriform-fossa conduit 92 in the cuff formation compares to a soft 26 Fr size nasopharyngeal airway; such soft nasopharyngeal airways are designed with softness that allows passage through a patient's nares without causing trauma to this delicate air passage while at the same time the nasopharyngeal airway is constructed to maintain a patent lumen after it has been inserted. A piriform-fossa conduit 92 comparable to such soft nasopharyngeal airway can easily withstand 60 cm $H_2O$ without collapse.

After the mask portion of the laryngeal mask is inserted into the pharynx of an unconscious patient and especially if the muscle tone of the pharynx returns, it is possible that the pharyngeal musculature and lower pharynx could exert a squeezing pressure on the distal portions of the mask portion 61 and that the piriform-fossa conduit itself might partially collapse. One advantage of such a soft and flexible piriform-fossa conduit is that it is compliant and be partially compressed by such external forces; and such partially compressed piriform-fossa conduit can still serve to direct insertion of orogastric tubes or medical instruments from outside the patient directly to the esophageal inlet as such well-lubricated tubes and instruments will be able to stent open such a partially collapsed passageway. Such partial collapse of the piriform-fossa conduit 92 can be an advantage to avoid mucosal injury and trauma and to avoid injury to the nerves of the tongue, pharynx, and larynx.

In the FIGURES of this disclosure, the piriform-fossa conduit 92 has been depicted on the left side of the laryngeal mask 60; following insertion into an unconscious patient the piriform-fossa conduit 92 would be on the left side of the patient's pharynx and travel through the left piriform fossa. This has two advantages.

The first advantage is a matter of practicality. In almost all anesthetizing locations the anesthesia and respiratory equipment is located to the right side of the patient head and neck; and the connection to the proximal orifice 72 of the airway tube takes place from the right side of the patient's head and neck. Placing the piriform-fossa conduit 92 of the left side of the laryngeal mask 60 prevents the piriform-fossa conduit 92 from interfering with airway tubing connection to respiratory equipment; and inserting orogastric tubes or medical instruments into the proximal orifice of the piriform-fossa conduit 92 will not interfere with airway tubing connection to respiratory equipment.

A second advantage for location on the left side of the laryngeal mask 60 concerns possible injury to the nerves supplying the vocal cords. Any artificial airway device including all embodiments of laryngeal masks have the small but distinct possibility of injury to the laryngeal nerves controlling the vocal cords. When such nerves are injured or paralyzed, it can become difficult or impossible for the patient to breath satisfactorily while awake. With a piriform-fossa conduit 92, even one constructed of soft and flexible material, it is possible that there would be a greater risk of nerve injury to the patient on the side of the piriform-fossa conduit 92 compared to the other side. In the general population, there already exists a greater incidence of palsy or paralysis of the left vocal cord compared to the right vocal cord. With such preferred position of the piriform-fossa conduit 92 on the left side of the laryngeal mask 60, there would be a smaller chance for a patient to emerge from anesthesia with bilateral (both sides) vocal cord paralysis. In alternative embodiments, however, the piriform-fossa conduit 92 an be positioned on the opposite (right) side of the laryngeal mask 60.

In particular embodiments of a laryngeal mask 60 with a piriform-fossa conduit 92, the segment of the piriform-fossa conduit 92 proximal to the mask portion 61 and emerging from the patient's mouth can be constructed from a stiffer and less flexible material compared to the segment of piriform-fossa conduit 92 in the cuff formation. Two such dissimilar segments can be joined at the mount coupling 102. One advantage of a stiffer and less flexible material for the segment of piriform-fossa conduit 92 emerging from the mouth is that it would facilitate insertion of the mask 60 into the pharynx and to advance the mask 60 into the esophageal inlet as a very flexible conduit drapes on top of the teeth and creates excessive friction during insertion; and such a stiffer conduit would also facilitate insertion of orogastric tubes and medical instruments into the proximal orifice 90.

The piriform-fossa conduit 92 may be bonded for a portion of its length to the airway tube 62; or the laryngeal mask 60 can be manufactured in such manner that they travel together and alongside each other. In a particular embodiment, a significant length of the piriform-fossa conduit 92 proximal to the mask portion 61 is not bonded to the airway tube 62; and since such a segment is an independent tube, there will be more freedom introducing the mask 60 into the patient's mouth and pharynx. To ease such insertion of the mask 60 into the mouth the piriform-fossa conduit 92 can be secured by mount coupling 102 proximate the proximal end of the mask portion 61 thereby creating a narrow waist of the airway tube 62 and piriform fossa conduit 92 proximate the proximal end of the mask portion 61 making it easier to introduce and advance the laryngeal mask 60 through the oral aperture.

Previous inventions of laryngeal masks with drainage and evacuation tubes have included enhanced modification of the cuff formation to increase the seal pressure with the pharyngeal and esophageal mucosal walls. The enhanced construction of the cuff formation and increased seal pressures can assure the advantages of these previous inventions.

In this disclosure, a laryngeal mask 60 with a piriform-fossa conduit 92 does not require an enhanced modification of the cuff formation to increase the seal pressure with the pharyngeal and esophageal mucosal walls. Such enhanced modifications of the cuff formation contribute to distortion of the laryngeal inlet 13 and narrowing of the glottis 30 and obstruction of the patient's airway; and the laryngeal mask 60 of this disclosure does not require such enhanced modifications of the cuff formation.

In describing embodiments of the invention, specific terminology is used for the sake of clarity. For the purpose of description, specific terms are intended to at least include technical and functional equivalents that operate in a similar manner to accomplish a similar result. Additionally, in some instances where a particular embodiment of the invention includes a plurality of system elements or method steps, those elements or steps may be replaced with a single element or step; likewise, a single element or step may be replaced with a plurality of elements or steps that serve the same purpose. Further, where parameters for various properties or other values are specified herein for embodiments of the invention, those parameters or values can be adjusted up or down by $1/100^{th}$, $1/50^{th}$, $1/20^{th}$, $1/10^{th}$, $1/5^{th}$, $1/3^{rd}$, $1/2$-$2/3^{rd}$, $3/4^{th}$, $4/5^{th}$, $9/10^{th}$, $19/20^{th}$, $49/50^{th}$, $99/100^{th}$, etc. (or up by a factor of 1, 2, 3, 4, 5, 6, 8, 10, 20, 50, 100, etc.), or by rounded-off approximations thereof, unless otherwise specified. Moreover, while this invention has been shown and described with references to particular embodiments thereof, those skilled in the art will understand that various substitutions and alterations in form and details may be made therein without departing from the scope of the invention. Further still, other aspects, functions and advantages are also within the scope of the invention; and all embodiments of the invention need not necessarily achieve all of the advantages or possess all of the characteristics described above. Additionally, steps, elements and features discussed herein in connection with one embodiment can likewise be used in conjunction with other embodiments. The contents of references, including reference texts, journal articles, patents, patent applications, etc., cited throughout the text are hereby incorporated by reference in their entirety; and appropriate components, steps, and characterizations from these references may or may not be included in embodiments of this invention. Still further, the components and steps identified in the Background section are integral to this disclosure and can be used in conjunction with or substituted for components and steps described elsewhere in the disclosure within the scope of the invention. In method claims, where stages are recited in a particular order—with or without sequenced prefacing characters added for ease of reference—the stages are not to be interpreted as being temporally limited to the order in which they are recited unless otherwise specified or implied by the terms and phrasing.

What is claimed is:

1. An artificial airway device for insertion in a pharynx of an unconscious patient and to form a seal around a circumference of a laryngeal inlet of the patient, comprising:
    a mask portion having a proximal end in a proximal half, a distal end in a distal half, and a medial line extending from the proximal end to the distal end centrally through the mask portion, wherein the mask portion has a bowl structure that helps to define a bowl interior concave toward an anterior-facing opening and a cuff formation attached circumferentially to a generally elliptical periphery of the bowl structure, wherein the generally elliptical periphery approximates a circumference of the laryngeal inlet when the mask is properly inserted in the pharynx; and
    an airway conduit with a proximal orifice and a distal orifice; and the distal orifice is coupled with and in fluid communication with the bowl interior in the proximal half of the mask portion, wherein
    the cuff formation includes a piriform-fossa conduit configured and positioned to travel around the laryngeal inlet and to pass through a piriform fossa of the patient when the mask is properly inserted in the pharynx, wherein the piriform-fossa conduit defines (a) a proximal orifice proximate the proximal orifice of the airway conduit and (b) a distal orifice along an outer perimeter of the cuff formation and confined to a distal one-third of the mask portion; wherein the piriform-fossa conduit is otherwise an airtight conduit; wherein an interior of the piriform-fossa conduit is non-intersecting with the medial line; wherein, in the distal half of the mask portion, the piriform-fossa conduit extends along a pathway to one side of the generally elliptical periphery; and wherein the proximal orifice and the distal orifice of the piriform-fossa conduit open to an exterior environment outside the artificial airway device.

2. The artificial airway device of claim 1, wherein an orogastric tube or medical instrument of sufficiently small diameter can be inserted into the proximal orifice of the piriform-fossa conduit, advanced though the length of the piriform-fossa conduit, and emerge from the distal orifice of the piriform-fossa conduit.

3. The artificial airway device of claim 1, wherein the cuff formation is inflatable.

4. The artificial airway device of claim 1, wherein, in the distal half of the mask portion, the cuff formation along the medial line is compressible to a thinner thickness under a common external pressure than is the cuff formation where the piriform-fossa conduit is present.

5. A method for installing an artificial airway in a patient, the method comprising:
    inserting an artificial airway device into the pharynx of an unconscious patient, wherein the artificial airway device has a mask portion having a proximal end in a proximal half, a distal end in a distal half, and a medial line extending from the proximal end to the distal end centrally through the mask portion, wherein the mask portion has a bowl structure that helps to define a bowl interior concave toward an anterior-facing opening and a cuff formation attached circumferentially to a generally elliptical periphery of the bowl structure, wherein the generally elliptical periphery approximates a circumference of the laryngeal inlet of the patient when the mask is properly inserted in the pharynx; and an airway conduit with a proximal orifice and a distal orifice; wherein the distal orifice is coupled with and in fluid communication with the bowl interior in the proximal half of the mask portion; wherein the cuff formation includes a piriform-fossa conduit that defines (a) a proximal orifice proximate the proximal orifice of the airway conduit and (b) a distal orifice along an outer perimeter of the cuff formation and confined to a distal one-third of the mask portion; wherein the piriform-fossa conduit is otherwise an airtight conduit; wherein an interior of the piriform-fossa conduit is non-intersecting with the medial line; wherein, in the distal one-half of the mask portion, the piriform-fossa conduit extends along a pathway to one side of the generally elliptical periphery; and wherein the proximal orifice and the distal orifice of the piriform-fossa conduit open to an exterior environment outside the artificial airway device;

advancing a tip of the artificial airway device within the patient's pharynx into the patient's esophageal inlet;

wherein the cuff formation occupies a space surrounding a circumference of the laryngeal inlet;

the bowl interior is aligned with the laryngeal inlet;

flowing gas including oxygen through the airway conduit into the bowl interior, from where the oxygen is delivered through the laryngeal inlet and through the patient's vocal cords to the patient's lungs;

positioning the piriform-fossa conduit in a piriform fossa of the patient;

positioning the proximal orifice of the piriform-fossa conduit outside the patient's mouth; and positioning the distal orifice of the piriform-fossa conduit within the patient's esophageal inlet.

6. The method of claim 5, further comprising directing insertion of an orogastric tube or medical instrument from outside the patient through the interior of the piriform-fossa conduit directly to the esophageal inlet and enabling advancement of the orogastric tube or medical instrument further into the esophagus or stomach of the patient.

7. The method of claim 6, further comprising using passive drainage or active suction to extract gastrointestinal fluids from the esophagus or stomach to an exterior of the patient.

8. The method of claim 5, wherein the artificial airway device further includes a plug, the method further comprising sealing the proximal orifice of the piriform-fossa conduit with the plug to prevent flow of gases through this conduit.

9. The method of claim 8, further comprising removing the plug and inserting an orogastric tube or medical instrument through the piriform-fossa conduit.

* * * * *